(12) United States Patent
Blain et al.

(10) Patent No.: US 9,456,855 B2
(45) Date of Patent: Oct. 4, 2016

(54) METHOD OF PLACING AN IMPLANT BETWEEN BONE PORTIONS

(71) Applicant: Spinal Elements, Inc., Carlsbad, CA (US)

(72) Inventors: Jason Blain, Encinitas, CA (US); Gregory Martin, Encinitas, CA (US); Charles C. Newton, San Diego, CA (US); Hyun Bae, Santa Monica, CA (US)

(73) Assignee: Spinal Elements, Inc., Carlsbad, CA (US)

( * ) Notice: Subject to any disclaimer, the term of this patent is extended or adjusted under 35 U.S.C. 154(b) by 0 days.

(21) Appl. No.: 14/491,820

(22) Filed: Sep. 19, 2014

(65) Prior Publication Data

US 2015/0094767 A1  Apr. 2, 2015

Related U.S. Application Data

(60) Provisional application No. 61/883,911, filed on Sep. 27, 2013.

(51) Int. Cl.
| | | |
|---|---|---|
| *A61B 17/88* | (2006.01) | |
| *A61B 17/70* | (2006.01) | |
| *A61B 17/82* | (2006.01) | |
| *A61B 17/16* | (2006.01) | |

(52) U.S. Cl.
CPC ....... *A61B 17/7064* (2013.01); *A61B 17/1642* (2013.01); *A61B 17/1671* (2013.01); *A61B 17/7053* (2013.01); *A61B 17/82* (2013.01); *A61B 17/1604* (2013.01)

(58) Field of Classification Search
CPC .......... A61B 17/7053; A61B 17/7062; A61B 17/7064; A61B 17/82; A61F 2/46; A61F 2/4603–2/4618; A61F 2/4611; A61F 2/4684
See application file for complete search history.

(56) References Cited

U.S. PATENT DOCUMENTS

| | | |
|---|---|---|
| 86,016 A | 1/1869 | Howell |
| 1,822,280 A | 9/1931 | Ervay |
| 1,822,330 A | 9/1931 | Anslie |

(Continued)

FOREIGN PATENT DOCUMENTS

| | | |
|---|---|---|
| CA | 2 437 575 | 4/2009 |
| DE | 93 04 368 | 5/1993 |

(Continued)

OTHER PUBLICATIONS

3rd Party Lab Notebook, "Facet Cartilage Repair," dated May 20, 2003 in 2 pages.

(Continued)

*Primary Examiner* — Jacqueline Johanas
(74) *Attorney, Agent, or Firm* — Knobbe, Martens, Olson & Bear, LLP

(57) ABSTRACT

Devices and methods for placing an implant between two bone portions are disclosed. In some embodiments, a method comprises disposing a portion of a flexible member through a first bone portion, through an aperture in a trial implant, and through a second bone portion. The trial implant can be withdrawn to enable an implant to be coupled to the flexible member. The method includes applying tension to the flexible member to urge the implant into the space between two bone portions. In some embodiments, the two bone portions are facets.

22 Claims, 23 Drawing Sheets

(56) References Cited

U.S. PATENT DOCUMENTS

| | | | |
|---|---|---|---|
| 2,486,303 A | 10/1949 | Longfellow |
| 3,111,945 A | 11/1963 | Von Solbrig |
| 3,570,497 A | 3/1971 | Lemole |
| 3,867,728 A | 2/1975 | Stubstad et al. |
| 3,875,595 A | 4/1975 | Froning |
| 3,879,767 A | 4/1975 | Stubstad |
| 4,001,896 A | 1/1977 | Arkangel |
| 4,037,603 A | 7/1977 | Wendorff |
| 4,085,466 A | 4/1978 | Goodfellow et al. |
| 4,119,091 A | 10/1978 | Partridge |
| 4,156,296 A | 5/1979 | Johnson et al. |
| 4,231,121 A | 11/1980 | Lewis |
| D261,935 S | 11/1981 | Halloran |
| 4,312,337 A | 1/1982 | Donohue |
| 4,349,921 A | 9/1982 | Kuntz |
| 4,502,161 A | 3/1985 | Wall |
| D279,502 S | 7/1985 | Halloran |
| D279,503 S | 7/1985 | Halloran |
| 4,535,764 A | 8/1985 | Ebert |
| 4,573,458 A | 3/1986 | Lower |
| 4,634,445 A | 1/1987 | Helal |
| 4,662,371 A | 5/1987 | Whipple et al. |
| 4,706,659 A | 11/1987 | Matthews et al. |
| 4,714,469 A | 12/1987 | Kenna |
| 4,722,331 A | 2/1988 | Fox |
| 4,730,615 A | 3/1988 | Sutherland et al. |
| 4,759,766 A | 7/1988 | Buettner-Janz et al. |
| 4,759,769 A | 7/1988 | Hedman et al. |
| 4,772,287 A | 9/1988 | Ray et al. |
| 4,773,402 A | 9/1988 | Asher et al. |
| 4,834,757 A | 5/1989 | Brantigan |
| 4,863,477 A | 9/1989 | Monson |
| 4,904,260 A | 2/1990 | Ray et al. |
| 4,907,577 A | 3/1990 | Wu |
| 4,911,718 A | 3/1990 | Lee et al. |
| 4,919,667 A | 4/1990 | Richmond |
| 4,923,471 A | 5/1990 | Morgan |
| 4,936,848 A | 6/1990 | Bagby |
| 4,941,466 A | 7/1990 | Romano |
| 4,959,065 A | 9/1990 | Arnett et al. |
| 4,969,909 A | 11/1990 | Barouk |
| 5,000,165 A | 3/1991 | Watanabe |
| 5,002,546 A | 3/1991 | Romano |
| 5,011,484 A | 4/1991 | Bréard |
| 5,015,255 A | 5/1991 | Kuslich |
| 5,047,055 A | 9/1991 | Bao et al. |
| 5,062,845 A | 11/1991 | Kuslich |
| 5,071,437 A | 12/1991 | Steffee |
| 5,092,866 A | 3/1992 | Breard et al. |
| 5,112,346 A | 5/1992 | Hiltebrandt et al. |
| 5,127,912 A | 7/1992 | Ray et al. |
| 5,147,404 A | 9/1992 | Downey |
| 5,171,280 A | 12/1992 | Baumgartner |
| 5,192,326 A | 3/1993 | Bao et al. |
| 5,209,755 A | 5/1993 | Abrahan et al. |
| 5,258,031 A | 11/1993 | Salib et al. |
| 5,300,073 A | 4/1994 | Ray et al. |
| 5,306,275 A | 4/1994 | Bryan |
| 5,306,308 A | 4/1994 | Gross et al. |
| 5,306,309 A | 4/1994 | Wagner et al. |
| 5,330,479 A | 7/1994 | Whitmore |
| 5,360,431 A | 11/1994 | Puno et al. |
| 5,368,596 A | 11/1994 | Brookhart |
| 5,370,697 A | 12/1994 | Baumgartner |
| 5,372,598 A | 12/1994 | Luhr et al. |
| 5,400,784 A | 3/1995 | Durand et al. |
| 5,401,269 A | 3/1995 | Buttner-Janz et al. |
| 5,413,576 A | 5/1995 | Rivard |
| 5,415,661 A | 5/1995 | Holmes |
| 5,425,773 A | 6/1995 | Boyd et al. |
| 5,437,672 A | 8/1995 | Alleyne |
| 5,445,639 A | 8/1995 | Kuslich et al. |
| 5,458,642 A | 10/1995 | Beer et al. |
| 5,458,643 A | 10/1995 | Oka et al. |
| 5,462,542 A | 10/1995 | Alesi, Jr. |
| 5,487,756 A | 1/1996 | Kallesoe et al. |
| 5,491,882 A | 2/1996 | Walston et al. |
| 5,496,318 A | 3/1996 | Howland et al. |
| 5,507,823 A | 4/1996 | Walston et al. |
| 5,514,180 A | 5/1996 | Heggeness et al. |
| 5,527,312 A | 6/1996 | Ray |
| 5,527,314 A | 6/1996 | Brumfield et al. |
| 5,534,028 A | 7/1996 | Bao et al. |
| 5,534,030 A | 7/1996 | Navarro et al. |
| 5,540,706 A | 7/1996 | Aust et al. |
| 5,545,229 A | 8/1996 | Parsons et al. |
| 5,549,619 A | 8/1996 | Peters et al. |
| 5,556,431 A | 9/1996 | Buttner-Janz |
| 5,562,738 A | 10/1996 | Boyd et al. |
| 5,571,131 A | 11/1996 | Ek et al. |
| 5,571,189 A | 11/1996 | Kuslich |
| 5,571,191 A | 11/1996 | Fitz |
| 5,577,995 A | 11/1996 | Walker et al. |
| 5,586,989 A | 12/1996 | Bray, Jr. |
| 5,591,165 A | 1/1997 | Jackson |
| 5,603,713 A | 2/1997 | Aust et al. |
| 5,638,700 A | 6/1997 | Shechter |
| 5,645,597 A | 7/1997 | Krapiva |
| 5,645,599 A | 7/1997 | Samani |
| 5,649,947 A | 7/1997 | Auerbach et al. |
| 5,653,762 A | 8/1997 | Pisharodi |
| 5,674,295 A | 10/1997 | Ray et al. |
| 5,674,296 A | 10/1997 | Bryan et al. |
| 5,676,701 A | 10/1997 | Yuan et al. |
| 5,683,464 A | 11/1997 | Wagner et al. |
| 5,683,466 A | 11/1997 | Vitale |
| 5,700,265 A | 12/1997 | Romano |
| 5,702,450 A | 12/1997 | Bisserie |
| 5,707,373 A | 1/1998 | Sevrain et al. |
| 5,716,415 A | 2/1998 | Steffee |
| 5,725,582 A | 3/1998 | Bevan et al. |
| 5,741,260 A | 4/1998 | Songer et al. |
| 5,741,261 A | 4/1998 | Moskovitz et al. |
| D395,138 S | 6/1998 | Ohata |
| 5,766,251 A | 6/1998 | Koshino |
| 5,766,253 A | 6/1998 | Brosnahan, III |
| 5,772,663 A | 6/1998 | Whiteside et al. |
| 5,797,916 A | 8/1998 | McDowell |
| 5,824,093 A | 10/1998 | Ray et al. |
| 5,824,094 A | 10/1998 | Serhan et al. |
| 5,836,948 A | 11/1998 | Zucherman et al. |
| 5,851,208 A | 12/1998 | Trott |
| 5,860,977 A | 1/1999 | Zucherman et al. |
| 5,865,846 A | 2/1999 | Bryan et al. |
| 5,868,745 A | 2/1999 | Alleyne |
| 5,876,404 A | 3/1999 | Zucherman et al. |
| 5,879,396 A | 3/1999 | Walston et al. |
| 5,888,203 A | 3/1999 | Goldberg |
| 5,893,889 A | 4/1999 | Harrington |
| 5,895,428 A | 4/1999 | Berry |
| RE36,221 E | 6/1999 | Breard et al. |
| 5,918,604 A * | 7/1999 | Whelan ............ A61B 17/0642 |
| | | 128/898 |
| 5,951,555 A | 9/1999 | Rehak et al. |
| 5,964,765 A | 10/1999 | Fenton et al. |
| 5,997,542 A | 12/1999 | Burke |
| 6,001,130 A | 12/1999 | Bryan et al. |
| 6,014,588 A | 1/2000 | Fitz |
| 6,019,763 A | 2/2000 | Nakamura et al. |
| 6,019,792 A | 2/2000 | Cauthen |
| 6,039,763 A | 3/2000 | Shelokov |
| 6,048,342 A | 4/2000 | Zucherman et al. |
| 6,050,998 A | 4/2000 | Fletcher |
| 6,063,121 A | 5/2000 | Xavier et al. |
| 6,066,325 A | 5/2000 | Wallace et al. |
| 6,068,630 A | 5/2000 | Zucherman et al. |
| RE36,758 E | 6/2000 | Fitz |
| 6,080,157 A | 6/2000 | Cathro et al. |
| 6,099,531 A | 8/2000 | Bonutti |
| 6,106,558 A | 8/2000 | Picha |
| 6,113,637 A | 9/2000 | Gill et al. |
| 6,132,464 A | 10/2000 | Martin |
| 6,132,465 A | 10/2000 | Ray et al. |
| 6,146,422 A | 11/2000 | Lawson |

(56) References Cited

U.S. PATENT DOCUMENTS

| | | | |
|---|---|---|---|
| 6,156,067 A | 12/2000 | Bryan et al. |
| 6,179,839 B1 | 1/2001 | Weiss et al. |
| D439,340 S | 3/2001 | Michelson |
| 6,200,322 B1 | 3/2001 | Branch et al. |
| 6,293,949 B1 | 9/2001 | Justis et al. |
| D450,122 S | 11/2001 | Michelson |
| 6,325,803 B1 | 12/2001 | Schumacher et al. |
| D454,953 S | 3/2002 | Michelson |
| 6,368,325 B1 | 4/2002 | McKinley et al. |
| 6,368,350 B1 | 4/2002 | Erickson et al. |
| 6,371,958 B1 | 4/2002 | Overaker |
| 6,375,573 B2 | 4/2002 | Romano |
| 6,379,386 B1 | 4/2002 | Resch et al. |
| D460,188 S | 7/2002 | Michelson |
| D460,189 S | 7/2002 | Michelson |
| 6,419,678 B1 | 7/2002 | Asfora |
| 6,419,703 B1 | 7/2002 | Fallin et al. |
| 6,436,099 B1 | 8/2002 | Drewry et al. |
| 6,436,101 B1 | 8/2002 | Hamada et al. |
| 6,436,146 B1 | 8/2002 | Hassler et al. |
| D463,560 S | 9/2002 | Michelson |
| 6,470,207 B1 | 10/2002 | Simon et al. |
| 6,565,605 B2 | 5/2003 | Goble et al. |
| 6,572,617 B1 | 6/2003 | Senegas |
| 6,579,318 B2 | 6/2003 | Varga et al. |
| 6,579,319 B2 | 6/2003 | Goble et al. |
| 6,589,244 B1 | 7/2003 | Sevrain et al. |
| 6,600,956 B2 | 7/2003 | Maschino et al. |
| 6,607,530 B1 | 8/2003 | Carl et al. |
| 6,610,091 B1 | 8/2003 | Reiley |
| D479,331 S | 9/2003 | Pike et al. |
| 6,626,944 B1 | 9/2003 | Taylor |
| 6,641,614 B1 | 11/2003 | Wagner et al. |
| 6,656,195 B2 | 12/2003 | Peters et al. |
| 6,669,697 B1 | 12/2003 | Pisharodi |
| 6,669,729 B2 | 12/2003 | Chin |
| 6,706,068 B2 | 3/2004 | Ferree |
| 6,743,232 B2 | 6/2004 | Overaker et al. |
| 6,761,720 B1 | 7/2004 | Senegas |
| 6,764,491 B2 | 7/2004 | Frey et al. |
| 6,770,095 B2 | 8/2004 | Grinberg et al. |
| 6,783,527 B2 | 8/2004 | Drewry et al. |
| 6,790,210 B1 | 9/2004 | Cragg et al. |
| 6,802,863 B2 | 10/2004 | Lawson et al. |
| 6,811,567 B2 | 11/2004 | Reiley |
| 6,902,566 B2 | 6/2005 | Zucherman et al. |
| 6,908,484 B2 | 6/2005 | Zubok et al. |
| 6,966,930 B2 | 11/2005 | Arnin et al. |
| 6,974,478 B2 | 12/2005 | Reiley et al. |
| 6,974,479 B2 | 12/2005 | Trieu |
| D517,404 S | 3/2006 | Schluter |
| 7,008,429 B2 | 3/2006 | Golobek |
| 7,013,675 B2 | 3/2006 | Marquez-Pickering |
| 7,051,451 B2 | 5/2006 | Augostino et al. |
| 7,074,238 B2 | 7/2006 | Stinson et al. |
| 7,101,375 B2 | 9/2006 | Zucherman et al. |
| 7,223,269 B2 | 5/2007 | Chappuis |
| D565,180 S | 3/2008 | Liao |
| 7,371,238 B2 | 5/2008 | Soboleski et al. |
| 7,458,981 B2 | 12/2008 | Fielding et al. |
| 7,517,358 B2 | 4/2009 | Petersen |
| 7,537,611 B2 | 5/2009 | Lee |
| 7,559,940 B2 | 7/2009 | McGuire et al. |
| 7,563,286 B2 | 7/2009 | Gerber et al. |
| 7,585,300 B2 | 9/2009 | Cha |
| 7,608,104 B2 | 10/2009 | Yuan et al. |
| 7,695,472 B2 | 4/2010 | Young |
| 7,799,077 B2 | 9/2010 | Lang et al. |
| 7,806,895 B2 | 10/2010 | Weier et al. |
| 7,846,183 B2 | 12/2010 | Blain |
| 7,862,590 B2 | 1/2011 | Lim et al. |
| 7,935,136 B2 | 5/2011 | Alamin et al. |
| D643,121 S | 8/2011 | Milford et al. |
| 7,993,370 B2 | 8/2011 | Jahng |
| 7,998,172 B2 | 8/2011 | Blain |
| 8,052,728 B2 | 11/2011 | Hestad |
| 8,109,971 B2 | 2/2012 | Hale |
| 8,133,225 B2 * | 3/2012 | Pieske ............... A61B 17/7233 606/62 |
| 8,163,016 B2 | 4/2012 | Linares |
| 8,192,468 B2 | 6/2012 | Biedermann et al. |
| 8,216,275 B2 | 7/2012 | Fielding et al. |
| 8,246,655 B2 | 8/2012 | Jackson et al. |
| 8,292,954 B2 | 10/2012 | Robinson et al. |
| 8,306,307 B2 | 11/2012 | Koike et al. |
| 8,394,125 B2 | 3/2013 | Assell |
| 8,579,903 B2 | 11/2013 | Carl |
| 8,652,137 B2 | 2/2014 | Blain et al. |
| 8,740,942 B2 | 6/2014 | Blain |
| 8,740,949 B2 | 6/2014 | Blain |
| 8,784,423 B2 * | 7/2014 | Kowarsch .......... A61B 17/1714 606/86 R |
| 8,858,597 B2 | 10/2014 | Blain |
| 8,882,804 B2 | 11/2014 | Blain |
| 8,961,613 B2 | 2/2015 | Assell et al. |
| D724,733 S | 3/2015 | Blain et al. |
| 8,992,533 B2 | 3/2015 | Blain et al. |
| 8,998,953 B2 | 4/2015 | Blain |
| 9,017,389 B2 | 4/2015 | Assell et al. |
| 9,060,787 B2 | 6/2015 | Blain et al. |
| D739,935 S | 9/2015 | Blain et al. |
| 9,149,283 B2 | 10/2015 | Assell et al. |
| 9,161,763 B2 | 10/2015 | Assell et al. |
| 9,179,943 B2 | 11/2015 | Blain |
| D748,262 S | 1/2016 | Blain |
| 9,233,006 B2 | 1/2016 | Assell et al. |
| D748,793 S | 2/2016 | Blain |
| 9,265,546 B2 | 2/2016 | Blain |
| 9,271,765 B2 | 3/2016 | Blain |
| 9,301,786 B2 | 4/2016 | Blain |
| 9,314,277 B2 | 4/2016 | Assell et al. |
| 2001/0018614 A1 | 8/2001 | Bianchi |
| 2002/0018799 A1 | 2/2002 | Spector et al. |
| 2002/0019637 A1 | 2/2002 | Frey et al. |
| 2002/0029039 A1 | 3/2002 | Zucherman et al. |
| 2002/0040227 A1 | 4/2002 | Harari |
| 2002/0065557 A1 | 5/2002 | Goble et al. |
| 2002/0072800 A1 | 6/2002 | Goble et al. |
| 2002/0077700 A1 | 6/2002 | Varga et al. |
| 2002/0086047 A1 | 7/2002 | Mueller et al. |
| 2002/0120335 A1 | 8/2002 | Angelucci et al. |
| 2002/0123806 A1 | 9/2002 | Reiley |
| 2002/0151895 A1 | 10/2002 | Soboleski et al. |
| 2002/0173800 A1 | 11/2002 | Dreyfuss et al. |
| 2002/0173813 A1 | 11/2002 | Peterson et al. |
| 2002/0198527 A1 | 12/2002 | Muckter |
| 2003/0004572 A1 | 1/2003 | Goble et al. |
| 2003/0028250 A1 | 2/2003 | Reiley et al. |
| 2003/0040797 A1 | 2/2003 | Fallin et al. |
| 2003/0120343 A1 * | 6/2003 | Whelan ............... A61B 17/0642 623/13.14 |
| 2003/0176919 A1 * | 9/2003 | Schmieding ....... A61B 17/0642 623/13.12 |
| 2003/0176922 A1 | 9/2003 | Lawson et al. |
| 2003/0187454 A1 | 10/2003 | Gill et al. |
| 2003/0191532 A1 | 10/2003 | Goble et al. |
| 2003/0204259 A1 | 10/2003 | Goble et al. |
| 2003/0216669 A1 | 11/2003 | Lang et al. |
| 2003/0233146 A1 | 12/2003 | Grinberg et al. |
| 2004/0006391 A1 | 1/2004 | Reiley |
| 2004/0010318 A1 | 1/2004 | Ferree |
| 2004/0024462 A1 | 2/2004 | Ferree et al. |
| 2004/0049271 A1 | 3/2004 | Biedermann et al. |
| 2004/0049272 A1 | 3/2004 | Reiley |
| 2004/0049273 A1 | 3/2004 | Reiley |
| 2004/0049274 A1 | 3/2004 | Reiley |
| 2004/0049275 A1 | 3/2004 | Reiley |
| 2004/0049276 A1 | 3/2004 | Reiley |
| 2004/0049277 A1 | 3/2004 | Reiley |
| 2004/0049278 A1 | 3/2004 | Reiley |
| 2004/0049281 A1 | 3/2004 | Reiley |
| 2004/0059429 A1 | 3/2004 | Amin et al. |
| 2004/0087954 A1 | 5/2004 | Allen et al. |
| 2004/0116927 A1 | 6/2004 | Graf |

(56) References Cited

U.S. PATENT DOCUMENTS

| | | |
|---|---|---|
| 2004/0127989 A1 | 7/2004 | Dooris et al. |
| 2004/0143264 A1 | 7/2004 | McAfee |
| 2004/0176844 A1 | 9/2004 | Zubok et al. |
| 2004/0199166 A1* | 10/2004 | Schmieding ....... A61B 17/1617 606/79 |
| 2004/0215341 A1 | 10/2004 | Sybert et al. |
| 2004/0230201 A1 | 11/2004 | Yuan et al. |
| 2004/0230304 A1 | 11/2004 | Yuan et al. |
| 2005/0010291 A1 | 1/2005 | Stinson et al. |
| 2005/0015146 A1 | 1/2005 | Louis et al. |
| 2005/0043797 A1 | 2/2005 | Lee |
| 2005/0043799 A1 | 2/2005 | Reiley |
| 2005/0049705 A1 | 3/2005 | Hale et al. |
| 2005/0055096 A1 | 3/2005 | Serhan et al. |
| 2005/0059972 A1 | 3/2005 | Biscup |
| 2005/0131409 A1 | 6/2005 | Chervitz et al. |
| 2005/0131538 A1 | 6/2005 | Chervitz et al. |
| 2005/0143818 A1 | 6/2005 | Yuan et al. |
| 2005/0159746 A1 | 7/2005 | Grob et al. |
| 2005/0197700 A1 | 9/2005 | Boehm et al. |
| 2005/0216017 A1 | 9/2005 | Fielding et al. |
| 2005/0251256 A1 | 11/2005 | Reiley |
| 2005/0256494 A1 | 11/2005 | Datta |
| 2006/0004367 A1 | 1/2006 | Alamin et al. |
| 2006/0036323 A1 | 2/2006 | Carl et al. |
| 2006/0041311 A1 | 2/2006 | McLeer |
| 2006/0084985 A1 | 4/2006 | Kim |
| 2006/0085072 A1 | 4/2006 | Funk et al. |
| 2006/0111782 A1 | 5/2006 | Petersen |
| 2006/0116684 A1* | 6/2006 | Whelan .............. A61B 17/0642 623/13.14 |
| 2006/0149375 A1 | 7/2006 | Yuan et al. |
| 2006/0200137 A1 | 9/2006 | Soboleski et al. |
| 2006/0241601 A1 | 10/2006 | Trautwein et al. |
| 2006/0241758 A1 | 10/2006 | Peterman et al. |
| 2006/0293691 A1 | 12/2006 | Mitra et al. |
| 2007/0055236 A1 | 3/2007 | Hudgins et al. |
| 2007/0078464 A1 | 4/2007 | Jones et al. |
| 2007/0118218 A1 | 5/2007 | Hooper |
| 2007/0149976 A1 | 6/2007 | Hale et al. |
| 2007/0179619 A1 | 8/2007 | Grab |
| 2007/0250166 A1 | 10/2007 | McKay |
| 2007/0270812 A1 | 11/2007 | Peckham |
| 2008/0009866 A1 | 1/2008 | Alamin et al. |
| 2008/0058929 A1* | 3/2008 | Whelan .............. A61B 17/0642 623/13.14 |
| 2008/0177264 A1 | 7/2008 | Alamin et al. |
| 2008/0183211 A1 | 7/2008 | Lamborne et al. |
| 2008/0228225 A1 | 9/2008 | Trautwein et al. |
| 2008/0287996 A1 | 11/2008 | Soholeski et al. |
| 2009/0005818 A1 | 1/2009 | Chin et al. |
| 2009/0018662 A1 | 1/2009 | Pasquet et al. |
| 2009/0024166 A1 | 1/2009 | Carl et al. |
| 2009/0076617 A1 | 3/2009 | Ralph et al. |
| 2009/0125066 A1 | 5/2009 | Kraus et al. |
| 2009/0138048 A1 | 5/2009 | Baccelli et al. |
| 2009/0171360 A1* | 7/2009 | Whelan .............. A61B 17/0642 606/88 |
| 2009/0198282 A1 | 8/2009 | Fielding et al. |
| 2009/0264928 A1 | 10/2009 | Blain |
| 2009/0264929 A1 | 10/2009 | Alamin et al. |
| 2009/0270918 A1 | 10/2009 | Attia et al. |
| 2010/0010548 A1* | 1/2010 | Hermida Ochoa ............ A61B 17/06066 606/86 A |
| 2010/0185241 A1 | 7/2010 | Malandain et al. |
| 2010/0204732 A1 | 8/2010 | Aschmann et al. |
| 2010/0234894 A1 | 9/2010 | Alamin et al. |
| 2010/0274289 A1 | 10/2010 | Carls et al. |
| 2010/0298829 A1 | 11/2010 | Schaller et al. |
| 2010/0318133 A1 | 12/2010 | Tornier |
| 2011/0022089 A1 | 1/2011 | Assell et al. |
| 2011/0040301 A1 | 2/2011 | Blain et al. |
| 2011/0098816 A1 | 4/2011 | Jacob et al. |
| 2011/0172712 A1 | 7/2011 | Chee et al. |
| 2011/0295318 A1 | 12/2011 | Alamin et al. |
| 2011/0313456 A1 | 12/2011 | Blain |
| 2012/0035658 A1 | 2/2012 | Goble et al. |
| 2012/0046749 A1 | 2/2012 | Tatsumi |
| 2012/0101502 A1 | 4/2012 | Kartalian et al. |
| 2012/0150231 A1 | 6/2012 | Alamin et al. |
| 2012/0221048 A1 | 8/2012 | Blain |
| 2012/0221049 A1 | 8/2012 | Blain |
| 2012/0245586 A1 | 9/2012 | Lehenkari et al. |
| 2012/0271354 A1 | 10/2012 | Baccelli et al. |
| 2012/0310244 A1 | 12/2012 | Blain et al. |
| 2013/0023878 A1 | 1/2013 | Belliard et al. |
| 2013/0041410 A1 | 2/2013 | Hestad et al. |
| 2013/0325065 A1 | 12/2013 | Malandain et al. |
| 2014/0228883 A1 | 8/2014 | Blain |
| 2014/0257397 A1 | 9/2014 | Akbarnia et al. |
| 2014/0277142 A1 | 9/2014 | Blain |
| 2014/0277148 A1 | 9/2014 | Blain |
| 2014/0277149 A1 | 9/2014 | Rooney et al. |
| 2014/0336653 A1 | 11/2014 | Bromer |
| 2015/0081023 A1 | 3/2015 | Blain |
| 2015/0094766 A1 | 4/2015 | Blain et al. |
| 2015/0094767 A1* | 4/2015 | Blain ................ A61B 17/7064 606/247 |
| 2015/0119988 A1 | 4/2015 | Assell et al. |
| 2015/0164516 A1 | 6/2015 | Blain et al. |
| 2015/0164652 A1 | 6/2015 | Assell et al. |
| 2015/0190149 A1 | 7/2015 | Assell et al. |
| 2015/0196330 A1 | 7/2015 | Blain |
| 2015/0257770 A1 | 9/2015 | Assell et al. |
| 2015/0257773 A1 | 9/2015 | Blain |
| 2015/0327872 A1 | 11/2015 | Assell et al. |
| 2016/0051294 A1 | 2/2016 | Blain |
| 2016/0128739 A1 | 5/2016 | Blain et al. |

FOREIGN PATENT DOCUMENTS

| | | |
|---|---|---|
| DE | 201 12 123 | 9/2001 |
| DE | 101 35 771 | 2/2003 |
| EP | 0 238 219 | 9/1987 |
| EP | 0 322 334 | 6/1989 |
| EP | 0 392 124 | 10/1990 |
| EP | 0 610 837 | 8/1994 |
| EP | 1 201 202 | 5/2002 |
| EP | 1 201 256 | 5/2002 |
| EP | 2 919 717 | 9/2015 |
| FR | 2 722 980 | 2/1996 |
| GB | 2 366 736 | 3/2002 |
| JP | 62-270147 | 11/1987 |
| JP | 10-179622 | 7/1998 |
| JP | 2004-508888 | 3/2004 |
| JP | 2007-503884 | 3/2007 |
| JP | 2007-190389 | 8/2007 |
| JP | 2007-521881 | 8/2007 |
| JP | 2008-510526 | 4/2008 |
| MX | 6012309 | 1/2007 |
| WO | WO 93/14721 | 8/1993 |
| WO | WO 94/04088 | 3/1994 |
| WO | WO 98/48717 | 11/1998 |
| WO | WO 99/23963 | 5/1999 |
| WO | WO 00/38582 | 7/2000 |
| WO | WO 00/53126 | 9/2000 |
| WO | WO 01/30248 | 5/2001 |
| WO | WO 02/45765 | 6/2002 |
| WO | WO 02/065954 | 8/2002 |
| WO | WO 02/096300 | 12/2002 |
| WO | WO 03/101350 | 12/2003 |
| WO | WO 2004/071358 | 8/2004 |
| WO | WO 2005/020850 | 3/2005 |
| WO | WO 2005/072661 | 8/2005 |
| WO | WO 2006/023980 | 3/2006 |
| WO | WO 2006/096803 | 9/2006 |
| WO | WO 2011/011621 | 1/2011 |
| WO | WO 2012/116266 | 8/2012 |
| WO | WO 2013/138655 | 9/2013 |

(56) References Cited

FOREIGN PATENT DOCUMENTS

| WO | WO 2014/078541 | 5/2014 |
|---|---|---|
| WO | WO 2016/044432 | 3/2016 |

OTHER PUBLICATIONS

ArthroTek, "CurvTek® Bone Tunneling System," Surgical Technique, 2000, pp. 6.
E-mail from 3rd Party citing Provisional U.S. Appl. Nos. 60/721,909; 60/750,005 and 60/749,000, initial e-mail dated May 11, 2009, reply e-mail dated May 18, 2009.
King et al., "Mechanism of Spinal Injury Due to Caudocephalad Acceleration," Symposium on the Lumbar Spine, Orthopedic Clinic of North America, Jan. 1975, vol. 6, pp. 19-31.
Parteq Innovations, "Facet Joint Implants & Resurfacing Devices," Technology Opportunity Bulletin, Tech ID 1999-012, Queen's University, Ontario Canada.
Official Communication in Australian Application No. 2005213459, dated Dec. 11, 2009.
Official Communication in Australian Application No. 2005213459, dated Dec. 15, 2010.
Official Communication in Australian Application No. 2011226832, dated Sep. 4, 2012.
Official Communication in Australian Application No. 2011226832, dated Oct. 31, 2012.
Official Communication in Australian Application No. AU2013237744, dated Sep. 2, 2014.
Official Communication in Canadian Application No. 2,555,355, dated Sep. 2, 2011.
Official Communication in Canadian Application No. 2,803,783, dated Sep. 29, 2014.
Official Communication in European Application No. 05712981.9, dated Jul. 24, 2007.
Official Communication in European Application No. 05712981.9, dated Mar. 10, 2008.
Official Communication in European Application No. 05712981.9, dated Apr. 6, 2009.
Official Communication in European Application No. 05712981.9, dated Jun. 15, 2010.
Official Communication in European Application No. 10178979.0, dated Mar. 14, 2011.
Official Communication in European Application No. 10178979.0, dated Nov. 13, 2012.
Official Communication in European Application No. 10178979.0, dated Aug. 5, 2013.
Official Communication in European Application No. 14175088.5, dated Sep. 8, 2014.
Official Communication in Japanese Application No. 2006-552309, dated May 25, 2010.
Official Communication in Japanese Application No. 2006-552309, dated Feb. 15, 2011.
Official Communication in Japanese Application No. 2010-221380, dated Feb. 15, 2011.
Official Communication in Japanese Application No. 2012-272106, dated Dec. 3, 2013.
Official Communication in Japanese Application No. 2012-272106, dated May 26, 2014.
International Search Report and Written Opinion in International Application No. PCT/US2005/003753, dated Dec. 5, 2006.
International Preliminary Report and Written Opinion in International App No. PCT/US2005/003753, dated Jan. 9, 2007.
Official Communication in European Application No. 08730413.5, dated Feb. 16, 2012.
Official Communication in European Application No. 14177951.2, dated Nov. 13, 2014.
International Search Report and Written Opinion in International Application No. PCT/US2008/054607, dated Jul. 10, 2008.
International Preliminary Report on Patentability in International Application No. PCT/US2008/054607, dated Sep. 3, 2009.
Official Communication in Australian Application No. 2011292297, dated Jul. 10, 2013.
Official Communication in European Application No. 11818586.7, dated Nov. 6, 2014.
International Search Report and Written Opinion in International Application No. PCT/US2011/047432, dated Dec. 12, 2011.
International Preliminary Report on Patentability in International Application No. PCT/US2011/047432, dated Feb. 28, 2013.
International Search Report in International Application No. PCT/US2012/026470, dated May 30, 2012.
International Preliminary Report on Patentability and Written Opinion in International Application No. PCT/US2012/026470, dated Sep. 6, 2013.
International Search Report and Written Opinion in International Application No. PCT/US2012/026472, dated Jun. 20, 2012.
International Preliminary Report on Patentability and Written Opinion in International Application No. PCT/US2012/026472, dated Mar. 20, 2014.
International Search Report and Written Opinion in International Application No. PCT/US2014/019325, dated Jun. 17, 2014.
International Search Report in International Application No. PCT/CA2002/000193 filed Feb. 15, 2002, dated Jun. 18, 2002.
International Preliminary Report on Patentability in International Application No. PCT/US2004/028094, filed Aug. 27, 2004.
International Search Report in International Application No. PCT/US2004/028094, filed Aug. 27, 2004.
International Search Report in International Application No. PCT/US2005/000987 filed Jan. 13, 2005, dated May 24, 2005.
International Preliminary Report on Patentability in International Application No. PCT/US2005/000987 filed Jan. 13, 2005, dated Jan. 17, 2006.
Notice of Acceptance in Australian Application No. AU2013237744, dated Apr. 23, 2015.
Official Communication in Canadian Application No. 2,803,783, dated Aug. 5, 2015.
Official Communication in Japanese Application No. 2012-272106, dated Feb. 23, 2015.
Official Communication in Japanese Application No. 2012-272106, dated Nov. 2, 2015.
Official Communication in Australian Application No. AU2012222229, dated Aug. 21, 2015.
Official Communication in Australian Application No. AU2012222230, dated Aug. 21, 2015.
International Search Report and Written Opinion in International Application No. PCT/US2014/019302, dated May 18, 2015.
International Preliminary Report on Patentability and Written Opinion in International Application No. PCT/US2014/019325, dated Sep. 24, 2015.
International Search Report and Written Opinion in International Application No. PCT/US2014/056598, dated Dec. 29, 2014.
International Preliminary Report on Patentability in International Application No. PCT/US2004/028094, dated Feb. 25, 2013.
Ash, H.E., "Proximal Interphalangeal Joint Dimensions for the Design of a Surface Replacement Prosthesis", School of Engineering, University of Durham, Proceedings of the Institution of Mechanical Engineers Part H Journal of Engineering in Medicine Feb. 1996, vol. 210, No. 2, pp. 95-108.
International Preliminary Report on Patentability and Written Opinion in International Application No. PCT/US2014/056598, dated Apr. 7, 2016.
International Search Report and Written Opinion in International Application No. PCT/US2015/050441, dated Dec. 28, 2015.
International Search Report and Written Opinion in International Application No. PCT/US2016/013062, dated Mar. 16, 2016.
Official Communication in Australian Application No. AU2015205875, dated Apr. 2, 2016.
Official Communication in European Application No. 14175088.5, dated Nov. 18, 2015.
Official Communication in Japanese Application No. 2013-524882, dated Mar. 2, 2015.
Official Communication in Japanese Application No. JP 2013-555591, dated Jan. 4, 2016.
Official Communication in Japanese Application No. JP 2013-555592, dated Dec. 7, 2015.

* cited by examiner

FIG. 3A
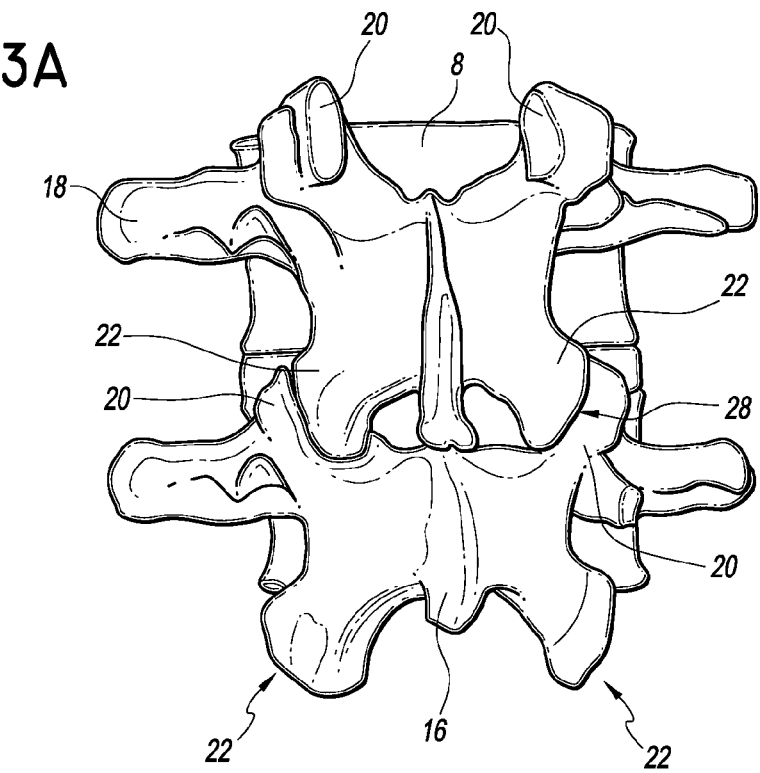
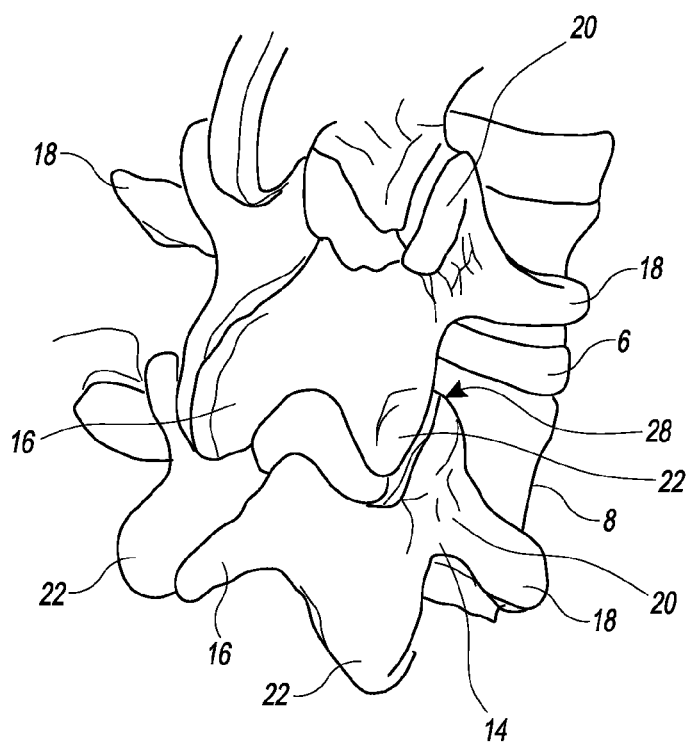
FIG. 3B

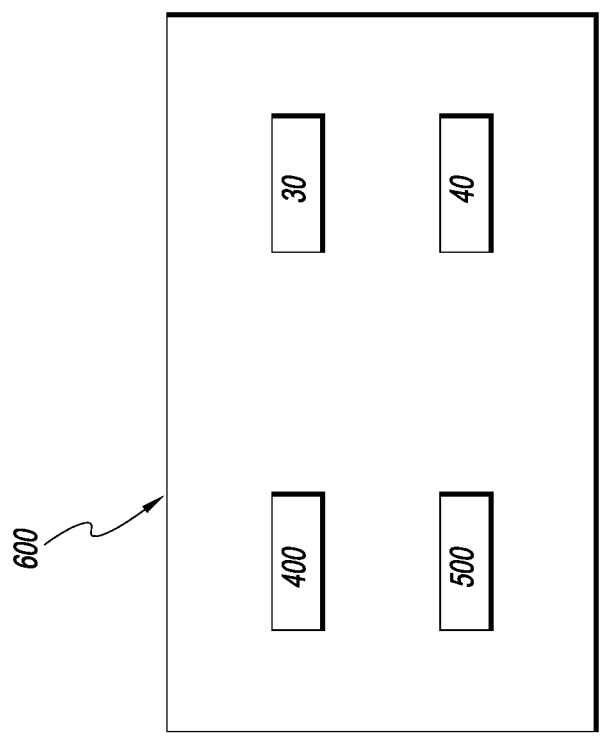

METHOD OF PLACING AN IMPLANT BETWEEN BONE PORTIONS

INCORPORATION BY REFERENCE TO ANY PRIORITY APPLICATIONS

This application claims priority under 35 U.S.C. §119(e) to U.S. Provisional Patent Application No. 61/883,911, filed Sep. 27, 2013, the disclosure of which is incorporated by reference herein in its entirety. This application incorporates by reference U.S. Pat. No. 8,740,949 (U.S. application Ser. No. 13/033,791, filed Feb. 24, 2011); U.S. Patent Publication 2012/0221049 (U.S. application Ser. No. 13/403,698, filed Feb. 23, 2012), U.S. Pat. No. 7,846,183 (application Ser. No. 10/865,073, filed Jun. 10, 2004), U.S. Pat. No. 8,652,137 (U.S. application Ser. No. 12/035,366, filed Feb. 21, 2008), U.S. Publication 2011/0040301 (application Ser. No. 12/859,009, filed Aug. 18, 2010), in their entirety.

BACKGROUND

Some embodiments described herein relate generally to methods and devices for facilitating the insertion of an implant between bone portions.

Some embodiments described herein relate generally to methods and implants for fusing bone, for example, fusing vertebrae by securing the articular processes of the vertebrae. Other embodiments described herein relate to augmentation and restoration of vertebral facet joints affected by degeneration and the surgical method and devices for implanting these devices in the spine Traumatic, inflammatory, and degenerative disorders of the spine can lead to severe pain and loss of mobility. One source of back and spine pain is related to degeneration of the facets of the spine or facet arthritis. Bony contact or grinding of degenerated facet joint surfaces can play a role in some pain syndromes. While many technological advances have focused on the intervertebral disc and artificial replacement or repair of the intervertebral disc, little advancement in facet repair has been made. Facet joint and disc degeneration frequently occur together. Thus, a need exists to address the clinical concerns raised by degenerative facet joints.

The current standard of care to address the degenerative problems with the facet joints is to fuse the two adjacent vertebrae. By performing this surgical procedure, the relative motion between the two adjacent vertebrae is stopped, thus stopping motion of the facets and any potential pain generated as a result thereof. Procedures to fuse two adjacent vertebrae often involve fixation and/or stabilization of the two adjacent vertebrae until the two adjacent vertebrae fuse. Commonly owned U.S. Patent Publications 2012/0221049 (U.S. application Ser. No. 13/403,698, filed Feb. 23, 2012) and U.S. Pat. No. 8,740,949 (U.S. application Ser. No. 13/033,791, filed Feb. 24, 2011) describe methods for stabilizing two bone portions by extending a flexible fastening band through a lumen in two bone portions. The flexible fastening band can be advanced through a fastener until the two bone portions are stabilized. In one embodiment, the first bone portion is the articular process of a first vertebra and the second bone portion is an articular process of a second vertebra. As described in these applications, in certain embodiments it is useful to dispose prosthesis (e.g., an allograft, metallic implant, etc.) between the first and second bone portions before stabilizing the two bone portions.

Commonly owned U.S. Pat. No. 7,846,183 (U.S. application Ser. No. 10/865,073, filed Jun. 10, 2004) describes a method in which the facet joint is restored by inserting a prosthesis between bone portions, such as a facet joint. Such a procedure can alleviate the bone on bone contact that is common in degenerative facet joints and often the source of pain generation, while allowing relative motion between the facets to continue post-operatively.

Injuries and/or surgical procedure on and/or effecting other bones can also result in the desire to fixate and/or stabilize a bone until the bone, or bone portions, can fuse, for example, to stabilize a sternum after heart surgery, to stabilize a rib after a break, etc. Current procedures to fixate and/or stabilize adjacent vertebrae and/or other bones can be slow and/or complex.

Accordingly, a need exists for an apparatus and a procedure to quickly and/or easily stabilize and/or fixate a bone.

SUMMARY

In some embodiments, a method of placing an implant between a first bone portion and a second bone portion is provided. The method can include the step of forming a lumen in a first bone portion. The method can include the step of forming a lumen in a second bone portion. The method can include the step of inserting a trial implant between the first bone portion and the second bone portion. The method can include the step of inserting a portion of a flexible member through the lumen in the first bone portion, through the trial implant, and through the lumen in the second bone portion. The method can include the step of withdrawing the trial implant and the flexible member from between the first and second bone portions. The method can include the step of coupling an implant with the flexible member. The method can include the step of advancing the implant between the first and second bone portions.

In some embodiments, the first bone portion is a first articular process and the second bone portion is a second articular process. The method can include the step of tying ends of the flexible member together. In some embodiments, the step of coupling an implant with the flexible member can include the step of passing the flexible member through a hole in the implant. In some embodiments, the step of coupling an implant with the flexible member can include the step of passing the flexible member through a slot extending from the edge of the implant. In some embodiments, the implant comprises an allograft. The method can include the step of sizing the implant to fit into the joint space between the first bone portion and the second bone portion. In some embodiments, the step of forming a lumen in a first bone portion can include drilling a hole. In some embodiments, the step of withdrawing the flexible member from between the first and second bone portion can include bringing the flexible member out at a joint line. The method can include the step of inserting the trial implant between the first bone portion and the second bone portion before forming a lumen in the first bone portion and forming a lumen in the second bone portion. In some embodiments, the step of advancing the implant between the first and second bone portions can include applying tension to both ends of the flexible member. The method can include the step of inserting a flexible retention member through the first bone portion, the implant, and the second bone portion and using the flexible retention member to secure the first bone portions and the second bone portions. In some embodiments, the flexible retention member comprises a ratchet.

In some embodiments, a method of placing an implant in a spine facet joint is provided. The method can include the step of drilling a hole across the facet joint. The method can include the step of inserting a trial implant in the joint space. The method can include the step of passing a flexible member through the hole and across the facet joint. The method can include the step of withdrawing the flexible member out of the facet joint at a joint line by withdrawing the trial implant. The method can include the step of coupling an implant with the flexible member. The method can include the step of pulling the ends of the flexible member to reduce implant into the joint space. In some embodiments, implant comprises an allograft. The method can include the step of sizing the implant to fit into the joint space.

In some embodiments, an implant for placement between a first bone portion and a second bone portion is provided. The implant can include a body that is sized to fit in the facet joint of a spine. In some embodiments, the body formed from artificial materials, allograft or a combination thereof. The implant can include the body having a slot extending from an edge of the body to a hole. In some embodiments, the slot and the hole are configured to slidingly accept a flexible member.

In some embodiments, a kit for placement of an implant between two bone portions is provided. The kit can include a trial member with an opening configured to engage a flexible member. The kit can include a drill configured to form an opening between two bone portions. In some embodiments, the drill is configured to drill a hole when the trial member inserted between the two bone portions. The kit can include an implant with an opening configured to engage the flexible member. The kit can include a flexible member. The kit can include a flexible fastening band through with fastener. In some embodiments, the implant comprises an allograft.

For purposes of summarizing the invention and the advantages achieved over the prior art, certain objects and advantages of the invention have been described herein above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught or suggested herein without necessarily achieving other objects or advantages as may be taught or suggested herein.

All of these embodiments are intended to be within the scope of the invention herein disclosed. These and other embodiments will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

These and other features, aspects, and advantages of the invention disclosed herein are described below with reference to the drawings of preferred embodiments, which are intended to illustrate and not to limit the invention.

FIG. 3A is a schematic posterior elevational view of a portion of the vertebral column.

FIG. 3B is a posterior-oblique elevational view of a portion of the vertebral column.

FIG. 22 is a block diagram of a kit according to an embodiment.

DETAILED DESCRIPTION

Although certain preferred embodiments and examples are disclosed below, it will be understood by those in the art that the invention extends beyond the specifically disclosed embodiments and/or uses of the invention and obvious modifications and equivalents thereof. Thus, it is intended that the scope of the invention herein disclosed should not be limited by the particular disclosed embodiments described below.

As used in this specification, the singular forms "a," "an" and "the" include plural referents unless the context clearly dictates otherwise. Thus, for example, the term "an implant" is intended to mean a single implant or a combination of implants. As used in this specification, a substance can include any biologic and/or chemical substance, including, but not limited to, medicine, adhesives, etc. While exemplary references are made with respect to vertebra, in some embodiments another bone or portions of bones can be involved. While specific reference may be made to a specific vertebra and/or subset and/or grouping of vertebrae, it is understood that any vertebra and/or subset and/or grouping, or combination of vertebrae can be used.

Figure 1:
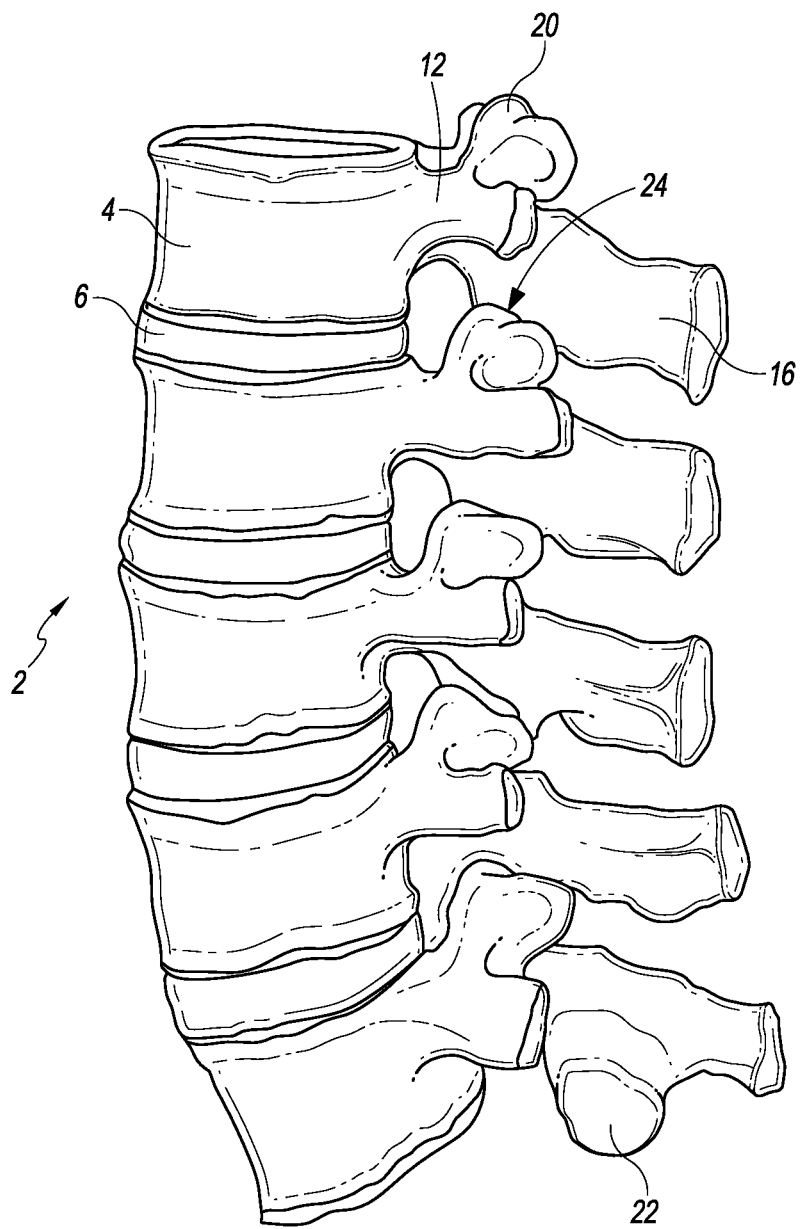
FIG. 1 is a lateral elevational view of a portion of the vertebral column.
Figure 2A:
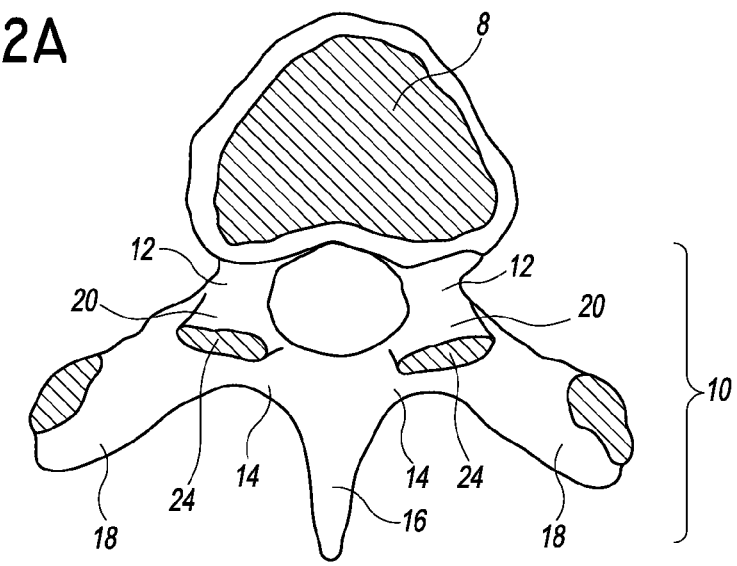
FIG. 2A is a schematic superior view of an isolated thoracic vertebra.
Figure 2B:
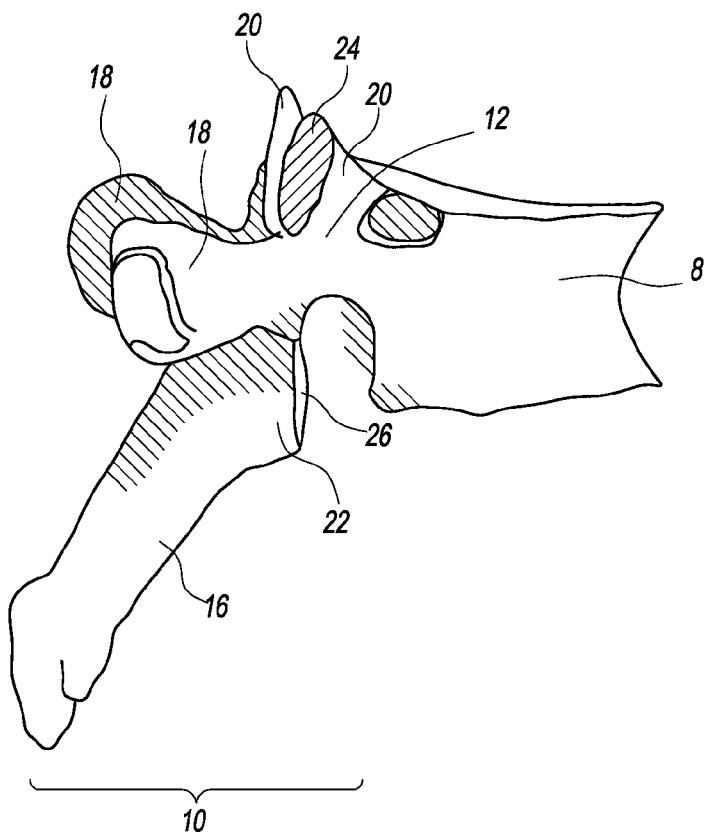
FIG. 2B are schematic side view of an isolated thoracic vertebra.
Figure 4A:
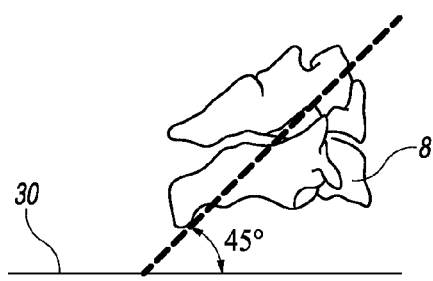
FIG. 4A is a schematic side view of a facet joint in the cervical vertebrae.
Figure 4B:
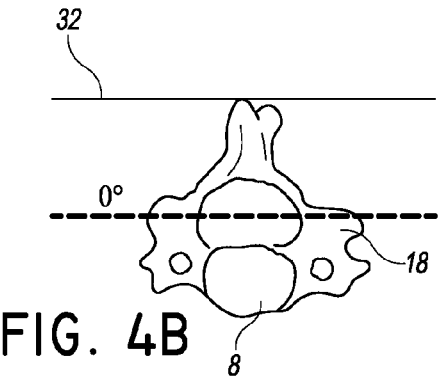
FIG. 4B is a schematic superior view of a facet joint in the cervical vertebrae.

As shown in FIG. 1, the vertebral column 2 comprises a series of alternating vertebrae 4 and fibrous discs 6 that provide axial support and movement to the upper portions of the body. The vertebral column 2 typically comprises thirty-three vertebrae 4, with seven cervical (C1-C7), twelve thoracic (T1-T12), five lumbar (L1-15), five fused sacral (S1-S5) and four fused coccygeal vertebrae. FIGS. 2A and 2B depict a typical thoracic vertebra. Each vertebra includes an anterior body 8 with a posterior arch 10. The posterior arch 10 comprises two pedicles 12 and two laminae 14 that join posteriorly to form a spinous process 16. Projecting from each side of the posterior arch 10 is a transverse 18, superior 20 and inferior articular process 22. The facets 24, 26 of the superior 20 and inferior articular processes 22 form facet joints 28 with the articular processes of the adjacent vertebrae (see FIGS. 3A and 3B). The facet joints are true synovial joints with cartilaginous surfaces and a joint capsule.

Figure 5A:
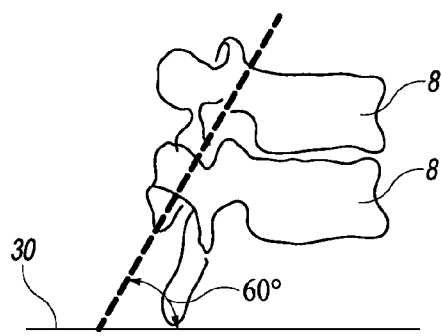
FIG. 5A is a schematic side view of a facet joint in the thoracic vertebrae.
Figure 5B:
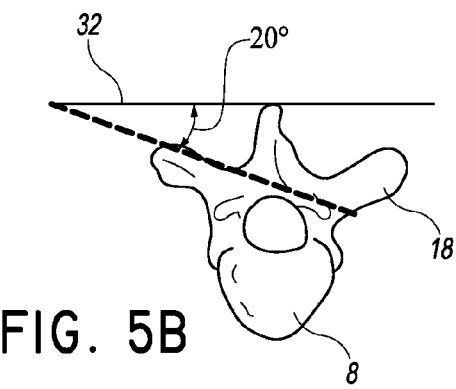
FIG. 5B is a schematic superior view of a facet joint in the thoracic vertebrae.
Figure 6A:
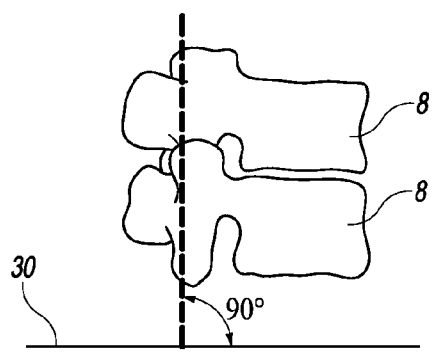
FIG. 6A is a schematic side view of a facet joint in the lumbar vertebrae.
Figure 6B:
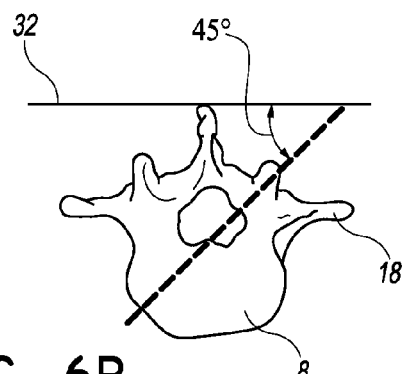
FIG. 6B is a schematic superior view of a facet joint in the lumbar vertebrae.

The orientation of the facet joints vary, depending on the level of the vertebral column. In the C1 and C2 vertebrae, for example the facet joints are parallel to the transverse plane. FIGS. 4A to 6B depict examples of the orientations of the facet joints at different levels of the vertebral column. In the C3 to C7 vertebrae examples shown in FIGS. 4A and 4B, the facets are oriented at a 45-degree angle to the transverse plane 30 and parallel to the frontal plane 32, respectively. This orientation allows the facet joints of the cervical vertebrae to flex, extend, lateral flex and rotate. At a 45-degree angle in the transverse plane 30, the facet joints of the cervical spine can guide, but do not limit, the movement of the cervical vertebrae. FIGS. 5A and 5B depict examples of the thoracic vertebrae, where the facets are oriented at a 60-degree angle to the transverse plane 30 and a 20-degree angle to the frontal plane 32, respectively. This orientation is capable of providing lateral flexion and rotation, but only limited flexion and extension. FIGS. 6A and 6B illustrate examples of the lumbar region, where the facet joints are oriented at 90-degree angles to the transverse plane 30 and a 45-degree angle to the frontal plane 32, respectively. The lumbar vertebrae are capable of flexion, extension and lateral flexion, but little, if any, rotation because of the 90-degree orientation of the facet joints in the transverse plane. The actual range of motion along the vertebral column can vary considerably with each individual vertebra.

In addition to guiding movement of the vertebrae, the facet joints also contribute to the load-bearing ability of the vertebral column. One study by King et al. Mechanism of Spinal Injury Due to Caudocephalad Acceleration, Orthop. Clin. North Am., 6:19 1975, found facet joint load-bearing as high as 30% in some positions of the vertebral column. The facet joints may also play a role in resisting shear stresses between the vertebrae. Over time, these forces acting on the facet joints can cause degeneration and arthritis.

Flexible Fastening Band

Figure 7:
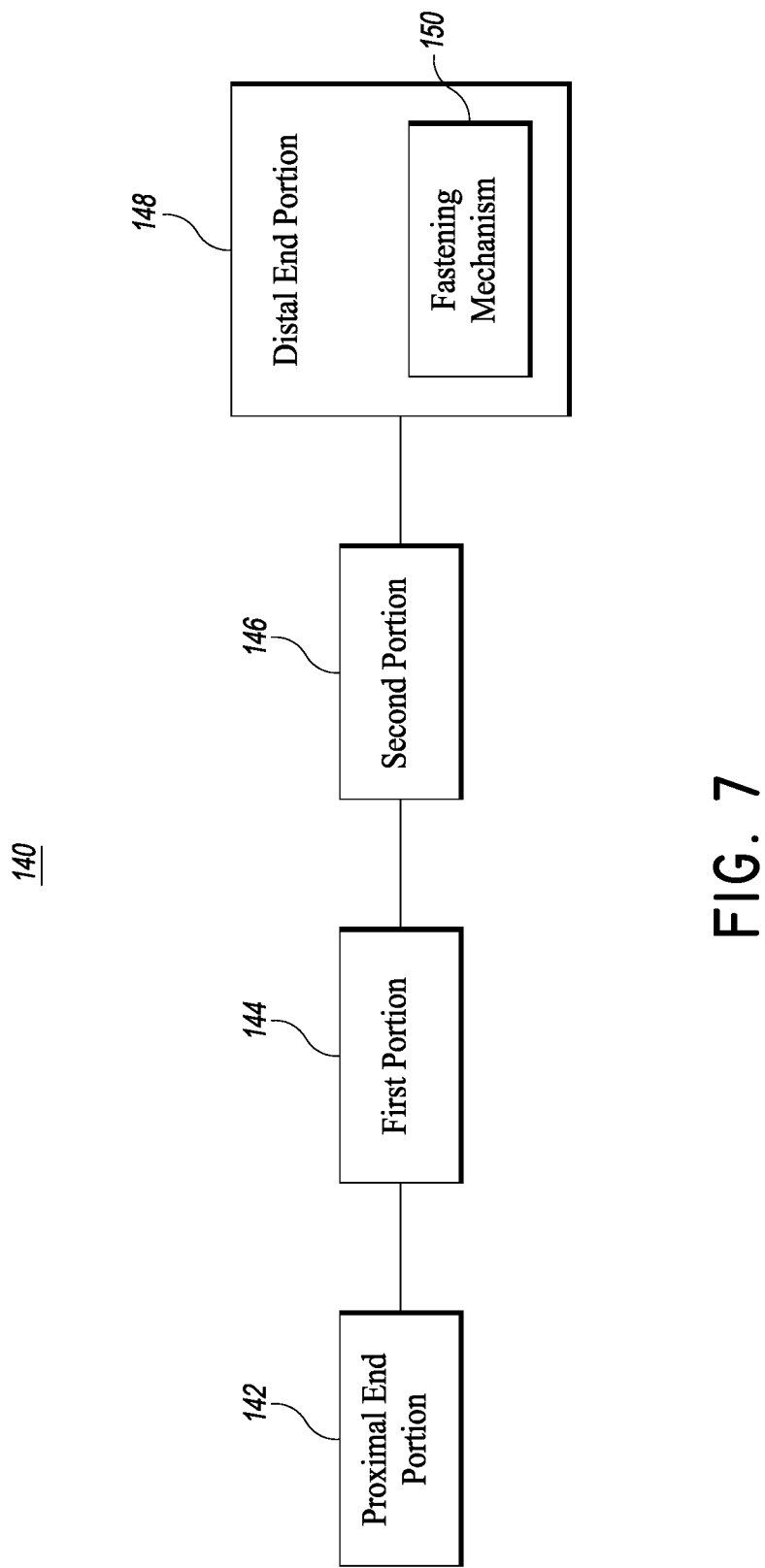
FIG. 7 is a block diagram of a flexible fastening band according to an embodiment.

In some embodiments described herein, a flexible fastening band can be used to stabilize and/or fixate a first vertebra to a second vertebra to reduce the pain, to reduce further degradation of a spine, or of a specific vertebra of a spine, and/or until the first vertebra and the second vertebra have fused. FIG. 7 depicts a block diagram of a flexible fastening band ("band") 140. Band 140 includes a flexible elongate body including a proximal end portion 142, a first portion 144, a second portion 146, and a distal end portion 148 that includes a fastening mechanism 150 (alternatively referred to herein as a fastener). In some embodiments, band 140 can include a third portion (not shown in FIG. 7). In some embodiments, band 140 can include a spacer (not shown in FIG. 7). In some embodiments, the fastening mechanism can be separate from the distal end portion. Band 140 can be configured to stabilize a first vertebra (not shown in FIG. 7) and/or a second vertebra (not shown in FIG. 7). Specifically, band 140 can be configured to stabilize the first vertebra and/or second vertebra by securing an articular process of the first vertebra to an articular process of a second vertebra. More specifically, band 140 can be configured to stabilize the first vertebra and/or a second vertebra by securing an articular process of the first vertebra to an articular process of a second vertebra by securing a facet of the articular process of the first vertebra with a facet of the articular process of the second vertebra. In some embodiments, band 140 can be removed from the vertebra, e.g. by cutting, breaking, or otherwise releasing band 140. In this manner, should a band fail, a replacement band can be inserted. Similarly, should the band be deemed ineffective for a particular patient, the band can be removed and an alternate treatment can be chosen without incurring permanent fusion of the vertebra. As will be described in more detail herein, band 140 can be monolithically formed or separately formed. Band 140 can include any biocompatible material, e.g., stainless steel, titanium, PEEK, nylon, etc.

Proximal end portion 142 is configured to pass through a lumen formed through a vertebra and a lumen formed through an adjacent vertebra, and to pass through fastening mechanism 150 of the distal end portion 148. In some embodiments, proximal end portion 142 can be shaped to increase the ease of inserting proximal end portion 142 into fastening mechanism 150, e.g., proximal end portion 142 can be tapered, rounded, and/or angled, etc., to reduce at least a portion of a cross-sectional area of proximal end portion 142.

First portion 144 can extend for a length between proximal end portion 142 and second portion 146, and can have a substantially uniform shape. The first portion 144 can have, for example, a substantially cuboidal shape, or a substantially cylindrical shape. In some embodiments, the length of first portion 144 can be more than twice the length of second portion 146. In some embodiments, the cross-sectional area of the first portion 144 can be smaller than the cross-sectional area of the second portion 146. In some embodiments, the cross-sectional area of first portion 144 can be less than a cross-sectional area of a lumen defined by the fastening mechanism 150. First portion 144 can include a gear rack (not shown in FIG. 7) configured to engage a ratchet (not shown in FIG. 7) of the fastening mechanism 150. The gear rack can be configured to allow first portion 144 to travel through fastening mechanism 150 in only one direction. First portion 144 can be monolithically formed with second portion 146. In some other embodiments, the first portion can be separately formed from the second portion. First portion 144 can be configured to be slideably disposed in a lumen of second portion 146.

Second portion 146 can have a length between first portion 144 and distal end portion 148, and can include a substantially uniform shape. In embodiments including the third portion, second portion 146 can have a length between first portion 144 and the third portion. Second portion 146 can have, for example, a substantially cuboidal shape or a substantially cylindrical shape. First portion 144 and second portion 146 can have the same or different shapes, e.g., first portion 144 and second portion 146 can both be substantially cuboidal (see, e.g., band 240 in FIG. 8), first portion 144 and second portion 146 can both be substantially cylindrical, first portion 144 can be substantially cuboidal while second portion 146 can be substantially cylindrical, or first portion 144 can be substantially cylindrical while second portion 146 can be substantially cuboidal (not shown). In some embodiments, the length of second portion 146 can be less than half the length of first portion 144. In some embodiments, the cross-sectional area of the second portion 146 can be greater than the cross-sectional area of the first portion 144. In some embodiments, the cross-sectional area of second portion 146 can be greater than a cross-sectional area of a lumen defined by the fastening mechanism 150. In this manner, as a portion of band 140 is advanced through fastening mechanism 150, the cross-sectional area of second portion 146 can prevent band 140 from advancing beyond the first portion 144. Second portion 146 can include a gear rack (not shown in FIG. 7) configured to engage the ratchet of the fastening mechanism 150. The gear rack can be configured to allow second portion 146 to travel through fastening mechanism 150 in only one direction. Second portion 146 can be monolithically formed with first portion 144. In some embodiments, the second portion can be separately formed from the first portion. Second portion 146 can define a lumen configured to slideably accept first portion 144.

Distal end portion 148 includes a fastening mechanism 150 configured to accept at least a portion of proximal end portion 142, first portion 144, and/or second portion 146. In some embodiments, distal end portion 148, second portion 146, first portion 144, and proximal end portion 142 can be monolithically formed. Fastening mechanism 150 includes a lumen (not shown in FIG. 7) configured to accept at least a portion of proximal end portion 142, a portion of first portion 142, and/or a portion of second portion 146. In some embodiments, the cross-sectional area of the lumen of fastening mechanism 150 is smaller than the cross-sectional area of second portion 146. In this manner, second portion 146 can be prevented from advancing through fastening mechanism 150.

In some embodiments, at least one of distal end portion 148, second portion 146, first portion 144, and proximal end portion 142 can be formed separately from the other(s) of distal end portion 148, second portion 146, first portion 144, and proximal end portion 142. Said another way, and by way of example, distal end portion 148, first portion 144, and proximal end portion 142 can be monolithically formed together, while second portion 146 can be separately formed. In this manner, band 140 can include an initial second portion 146 configured to be replaced and/or covered with a replacement second portion 146. By way of a first example, initial second portion 146 can be monolithically formed with first portion 144 and replacement second portion 146 can be slideably disposed over initial second portion 146. By way of a second example, initial second portion 146 can be separately formed from first portion 144, can be removed from band 140, and replacement second portion 146 can be slideably disposed over first portion 144. By way of a third example, initial second portion 146 can be separately or monolithically formed from first portion 144, and replacement second portion 146 can be slideably disposed over first portion 144 and initial second portion 146. In some embodiments, initial second portion 146 and replacement second portion 146 can have the same shape, e.g., initial second portion 146 can include a substantially cylindrical shape and replacement second portion 146 can include a substantially cylindrical shape. In some embodiments, initial second portion 146 and replacement second portion 146 can have different shapes, e.g., initial second portion 146 can include a substantially cuboidal shape and replacement second portion 146 can include a substantially cylindrical shape.

In some embodiments, the shape of first portion 144 and the shape of second portion 146 can be determined based on the shape of an artificial lumen formed through an articular process of a vertebra. By way of example, if the shape of the artificial lumen is cuboidal, the shape of the first portion 144 and the shape of the second portion 146 can be cuboidal to allow the first portion 144 and the second portion 146 to slideably advance through the artificial lumen. By way of a second example, if the shape of the artificial lumen is cylindrical, the shape of the first portion 144 and the shape of the second portion 146 can be either cuboidal or cylindrical. Continuing with the second example, the shape of the first portion 144 can be cuboidal to allow the first portion 144 to advance easily through the artificial lumen, while the shape of the second portion 146 can be cylindrical to allow the second portion 146 to fit more tightly within the artificial lumen as compared to a cuboidal shape.

In some embodiments, the shape of the first portion 144 and the shape of the second portion 146 can be determined based on characteristics of the bone or bone portion against which the first portion 144 and the second portion 146 may contact. By way of example, while first portion 144 and/or second portion 146 can be substantially cuboidal, edges of the first portion 144 and/or the second portion 146 can be rounded, partially rounded, and/or otherwise shaped to compliment the shape of a bone or bone portion, and/or to reduce digging or grinding into the bone or bone portion. In this manner, use of band 140 may cause little or no damage to the bone or bone portions contacted by band 140.

In some embodiments, band 140 can include a third portion (not shown in FIG. 7). The third portion can have a length between second portion 146 and distal end portion 150, and can have a substantially uniform shape. In some embodiments, the third portion can have, for example, a substantially cuboidal shape or a substantially cylindrical shape. In some embodiments, the length of the third portion can be less than half the length of first portion 144. The third portion can be monolithically formed with first portion 144 and/or the second portion 146. In some other embodiments, the first portion can be separately formed from the second portion and/or the first portion.

While each of first portion 144, second portion 146, and the third portion can be a substantially uniform shape, in some embodiments any one of first portion 144, second portion 146, and the third portion can include a transition portion to transition band 140 from a first substantially uniform shape to a second substantially uniform shape. By way of example, in some embodiments, first portion 144 and the third portion can be substantially cuboidal and second portion 146 can be substantially cylindrical. In this example, second portion 146 can include an angled, conical, or other shaped transition portion.

Figure 8:
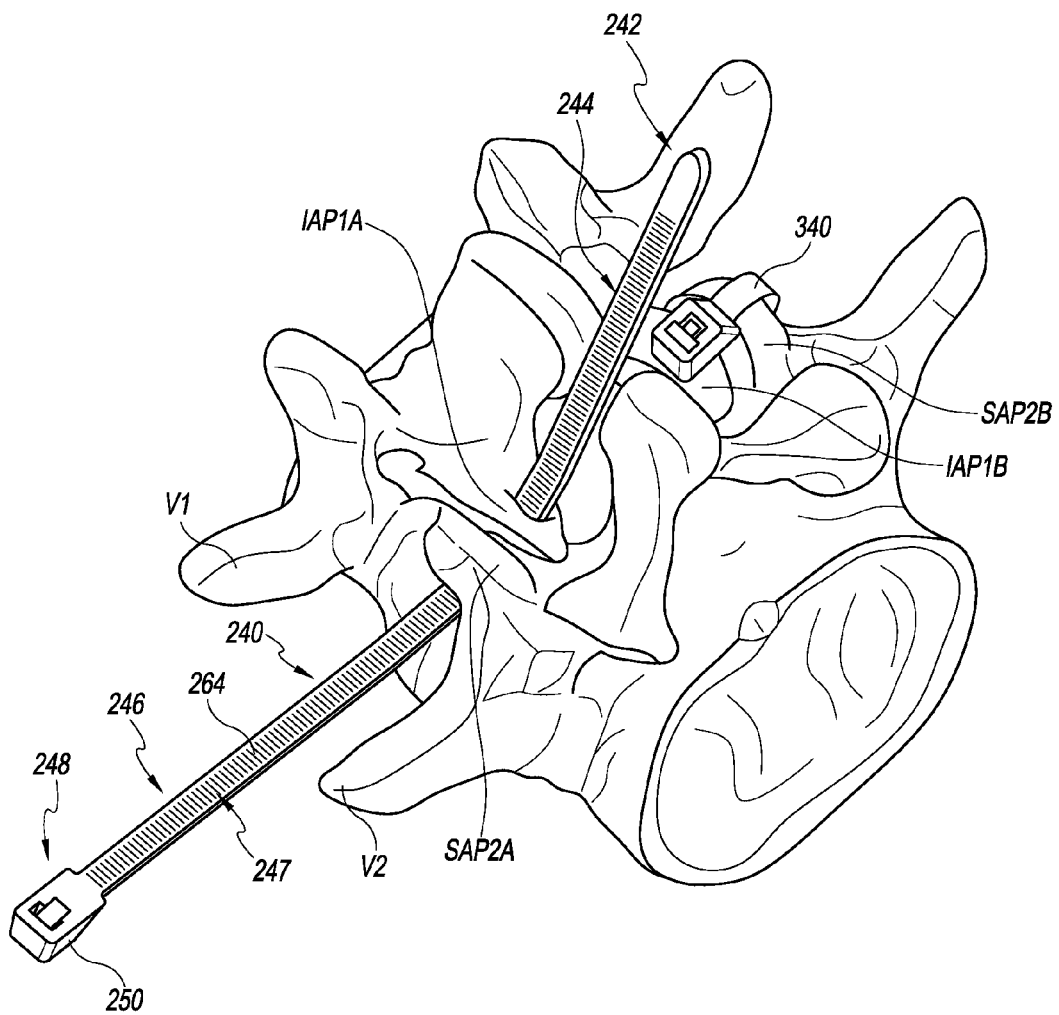
FIGS. 8-10 are posterior perspective views of a portion of the vertebral column depicting a method of stabilizing a vertebra using a flexible fastening band according to an embodiment.
Figure 9:
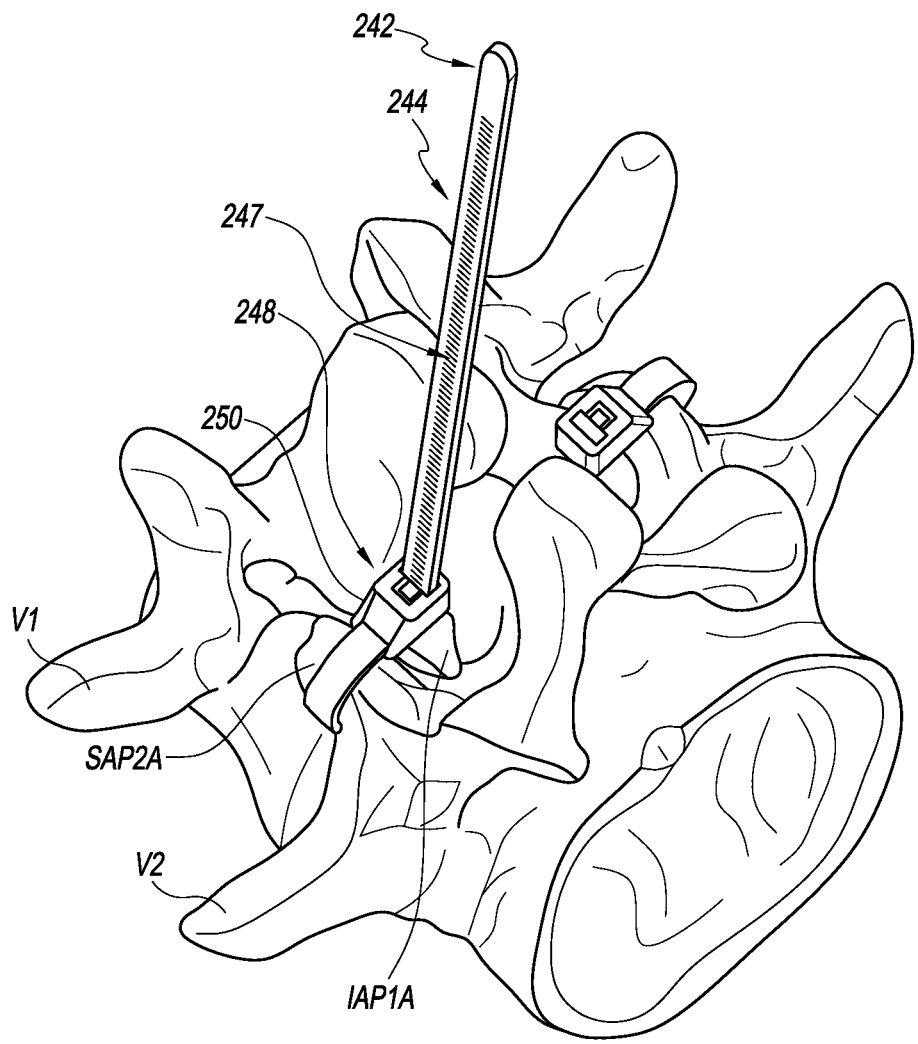
Figure 10:
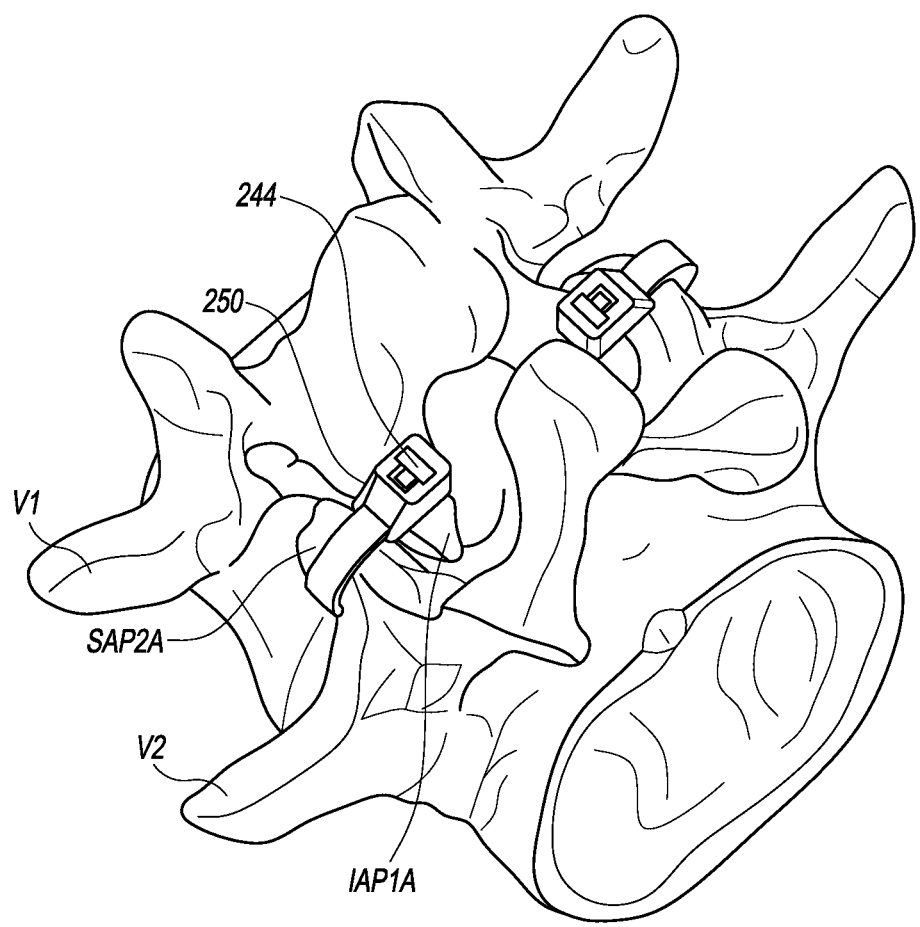

FIGS. 8-10 show posterior perspective views of a portion of the vertebral column during a method for stabilizing adjacent vertebrae using a flexible fastening band ("band") 240 according to an embodiment. As shown in FIG. 8, a band 240 can be used to stabilize a vertebra V1 and vertebra V2 via the inferior articular process IAP1A of vertebra V1 and the superior articular process SAP2A of vertebra V2. Also as shown in FIG. 8, a flexible fastening band ("band") 340 is used to stabilize a vertebra V1 and vertebra V2 via the inferior articular process IAP1B of vertebra V1 and the superior articular process SAP2B of vertebra V2. In some embodiments, vertebra V1 and/or vertebra V2 are stabilized using only one of band 240 or band 340. In some such embodiments, one of band 240 or band 340 can be used to stabilize vertebra V1 and/or vertebra V2 via one of via the inferior articular process IAP1A of vertebra V1 and the superior articular process SAP2A of vertebra V2, or, via the inferior articular process IAP1B of vertebra V1 and the superior articular process SAP2B of vertebra V2. In other such embodiments, one of band 240 or band 340 can be used to stabilize vertebra V1 and/or vertebra V2 via both of the inferior articular process IAP1A of vertebra V1 and the superior articular process SAP2A of vertebra V2, and, the inferior articular process IAP1B of vertebra V1 and the superior articular process SAP2B of vertebra V2.

Each of band 240 and band 340 can be similar to band 140 described above and can include similar components. By way of example, band 240 includes a proximal end portion 242, a first portion 244, a second portion 246, and a distal end portion 248 including a fastening mechanism 250, and band 340 includes a proximal end portion (not shown in FIG. 8), a first portion, a second portion, and a distal end portion including a fastening mechanism. As shown in FIGS. 8-10, the shapes of first portion 244, the first portion of band 340, second portion 246, and the second portion of band 340 can all be cuboidal. As shown in FIG. 8, band 240 includes a gear rack 247 and gears 264. Each of gears 264 can be wedge shaped to allow each of gears 264 to displace the ratchet of fastening mechanism 250 in only one direction. In some embodiments, gears 264 can be other shapes, such as blocks, etc.

Additional description, modified and alternative embodiments of the flexible fastening band and methods of installing and using such a band can be found in U.S. Pat. No. 8,740,949 (U.S. application Ser. No. 13/033,791, filed Feb. 24, 2011) and U.S. Patent Publication 2012/0221049 (U.S. application Ser. No. 13/403,698, filed Feb. 23, 2012), which are hereby bodily incorporated by reference.

Method and Apparatus for Placement of Device Between Bone Portions

Figure 11:
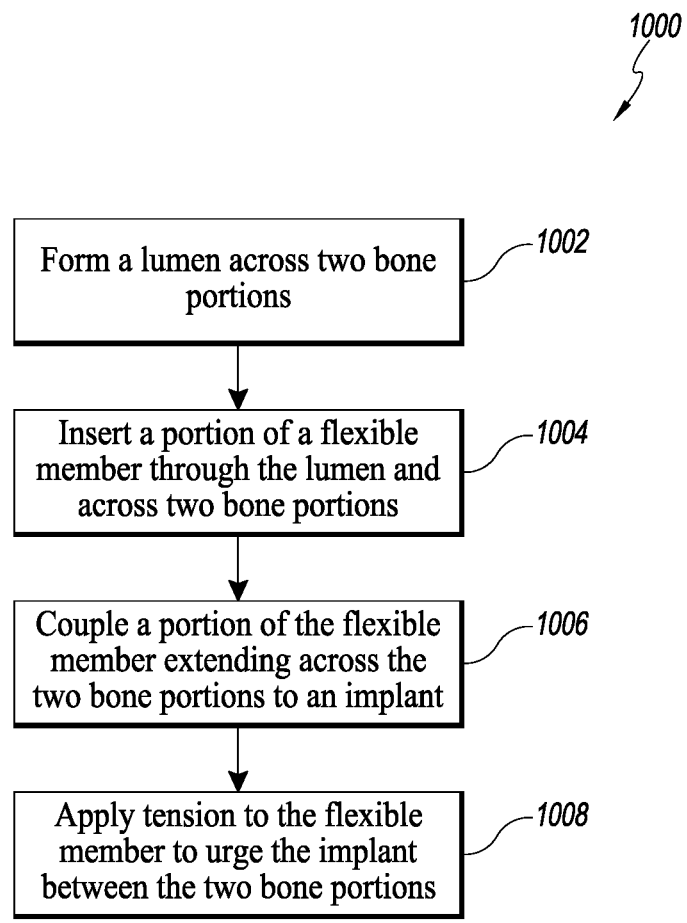
FIG. 11 is a flow chart illustrating a method of inserting an implant between two bone portions.

FIG. 11 depicts a flow chart illustrating a method 1000 of placing an implant between two bone portions. Prior to use of the implant, a patient can be prepared for surgery. Some examples of preparations for surgery are shown and described in U.S. Publication 2011/0040301 (application Ser. No. 12/859,009, filed Aug. 18, 2010) and U.S. Pat. No. 7,846,183 (application Ser. No. 10/865,073, filed Jun. 10, 2004). In addition to those procedures described in this application and others incorporated by reference, in some embodiments, the surgical procedure can include direct visualization of the vertebra(e) to be stabilized. Said another way, the medical practitioner can perform the operation without the use of fluoroscopy, and, in this manner, may not have to rely on the inaccuracies and/or inconvenience inherent in fluoroscopic procedures. This direct visualization can be possible due to the small incision necessary for implantation of the band, for example, less than about 25 mm, and due to the ease of implanting and deploying the band. In some embodiments, the surgical procedure used can include forming an opening in body tissue. In some embodiments, this opening is substantially equidistant between a first articular process of the first vertebra and a second articular process of the first vertebra. A cannula (not shown) can be inserted through the opening and a proximal end of the cannula can be positioned near the lumen of superior articular process SAP2A of vertebra V2.

Step 1002 can include forming a lumen across two bone portions. A drill or other device (e.g., tissue punch or reamer) can be used to form a lumen across two bone portions. In some embodiments, the two bone portions are facets. This step can involve forming a lumen in superior articular process SAP2A of vertebra V2 and inferior articular process IAP1A of vertebra V1. For example, the drill can be used to form the lumen in a facet of superior articular process SAP2A of vertebra V2 and form the lumen in a facet of inferior articular process IAP1A of vertebra V1. Methods and devices for forming lumens in vertebra are described in U.S. Pat. No. 7,846,183 (application Ser. No. 10/865,073, filed Jun. 10, 2004) and U.S. Patent Publication No. 2011/0040301 (application Ser. No. 12/859,009, filed Aug. 18, 2010), which are hereby bodily incorporated by reference herein. A flexible member, such as a suture, can be positioned within the cannula and can be advanced through the cannula until the proximal end portion of the flexible member is positioned near the lumen of superior articular process SAP2A of vertebra V2.

Step 1004 can include inserting a portion of the flexible member through the lumen and across the two bone portions. The flexible member can be inserted into and through the lumen of the first bone portion. The flexible member can be inserted into and through the lumen of the second bone portion. The flexible member has two ends. In some embodiments, the first end is threaded consecutively through the first bone portion and through the second bone portion. After the threading, one end of the flexible member extends beyond the first bone portion and the other end of the flexible member extends beyond the second bone portion. In some embodiments, the two bone portions are facets. The proximal end portion of the flexile member can be inserted into the lumen of superior articular process SAP2A of vertebra V2 and through the lumen of inferior articular process IAP1A of vertebra V1. After the threading, one end of the flexible member extends beyond the superior articular process and the other end of the flexible member extends beyond the inferior articular process.

Step 1006 can include coupling a portion of the flexible member extending across to bone portions to the implant. This step may include withdrawing a portion of the flexible member out of the joint. In some embodiments, the flexible member is coupled to a trial implant when the flexible member is withdrawn. This step can include bringing the flexible member out at a joint line. In some embodiments, the bone portions are facets. This step may include withdrawing a portion of the flexible member from the facet joint. An implant is coupled to the flexible member. In some embodiments, the implant can be coupled to the flexible member by sliding the implant onto the flexible member. The implant can include an engagement feature extending from the edge of the implant to the center of the implant. The engagement feature may be slot connected to an aperture. The slot may be linear or non-linear. A non-linear slot may prevent accidental disengagement between the implant and the flexible member. During step 1006, the flexible member remains threaded through the lumen in the first bone portion and the lumen of the second bone portion.

Step 1008 can include inserting the implant into the space between the bone portions. In some embodiments, the implant is inserted into the joint space between facet joints. In some embodiments, tension is applied to both ends of flexible member. The tension takes up slack in the flexible member, urging the implant into the joint space. Tension can be applied until the shortest distance of the flexible member is between the first bone portion and the second bone portion. The implant can be positioned such that the aperture of the implant forms a path between the first bone portion and the second bone portion.

With the implant between two bone portion, for example within the facet joint, a band can inserted into and through the lumen in first bone portion, into and through the aperture in the implant, and into and through the lumen in the second bone portion. The band or other retaining member can be advanced through a fastening mechanism until the two bone portions are stabilized as described in U.S. Patent Publication No. 2012/0221049 (U.S. application Ser. No. 13/403,698, filed Feb. 23, 2012) and U.S. Pat. No. 8,740,949 (U.S. application Ser. No. 13/033,791, filed Feb. 24, 2011). In such embodiments, the band can extend through the implant. The flexible member can be cut to reduce the size the flexible member. In some embodiments, the ends of the flexible member can be tied to secure the implant within the joint.

Figure 12:
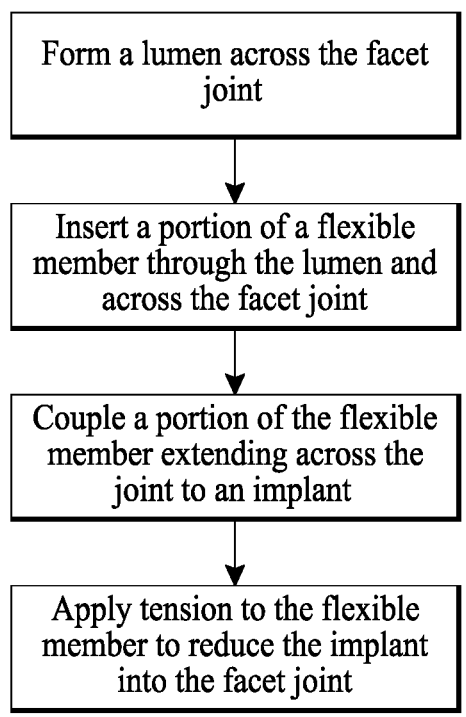
FIG. 12 is a flow chart illustrating a method of inserting an implant into a facet joint.

FIG. 12 is a flow chart illustrating a method of placing an implant within a facet joint. FIG. 12 shows a similar method to FIG. 11, wherein the first bone portion is a first facet and the second bone portion is a second facet. With respect to FIGS. 11 and 12 and the associated description above, it should be appreciated that not all steps are necessary and/or that the order of the steps rearranged and/or combined. For example, in certain arrangements, the flexible member can be extended across the facet joint (or two bone portions) while the lumen is being formed.

FIGS. 13-21 illustrate various method steps wherein the first bone portion is a first facet and the second bone portion is a second facet. As described above, prior the illustrated steps, a patient can be prepared for surgery and access can be provided to the treatment site.

Figure 13:
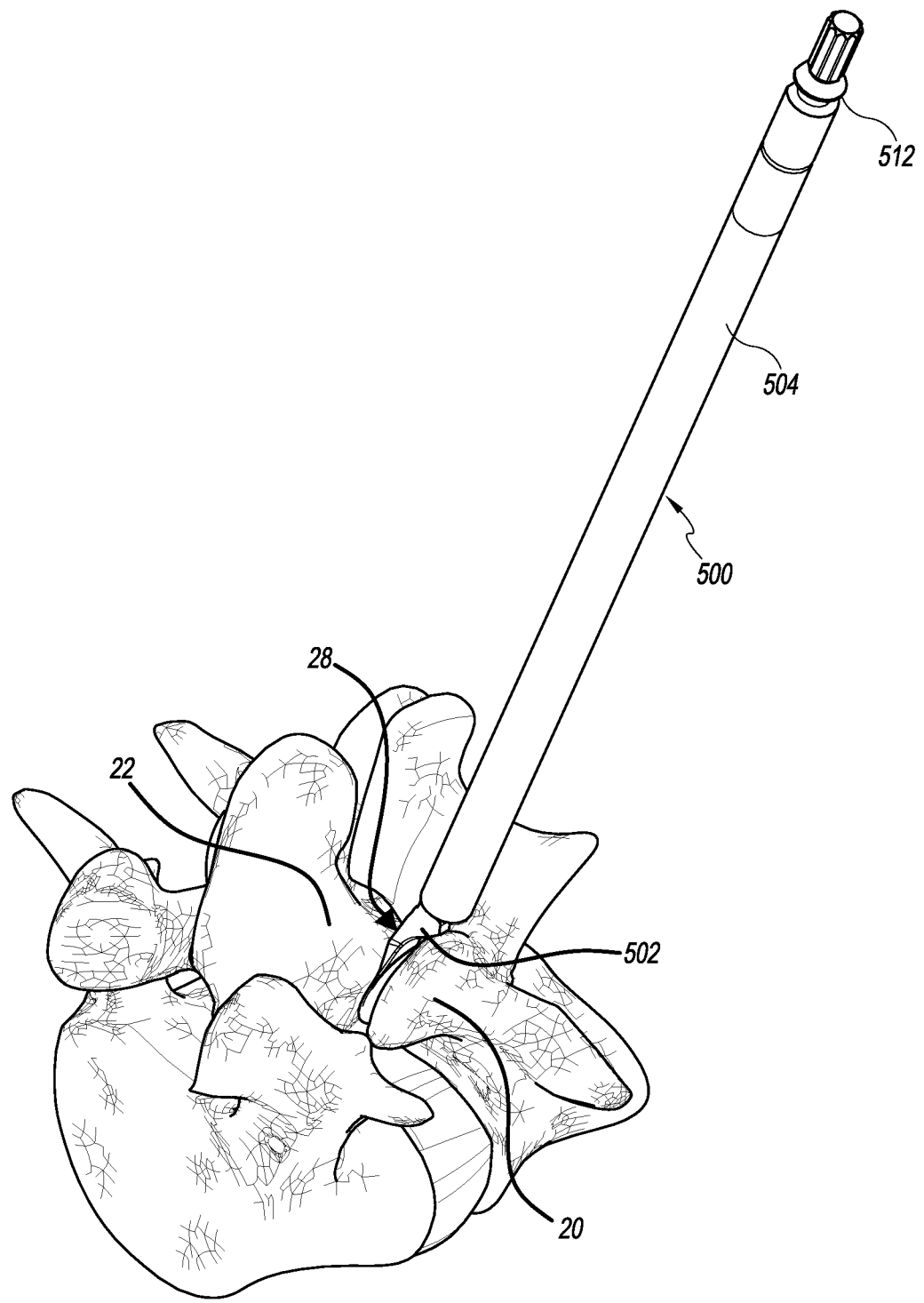
FIG. 13 is a schematic view of one embodiment of a trial member having a trial implant deployed in a facet joint.

FIG. 13 shows the trial member 500 inserted into the patient. In some embodiments, a trial implant 502 is inserted in the facet joint space between the articular processes 20, 22. In some embodiments, the trial implant 502 is inserted after the facet joint has been incised and the articular surfaces prepared. The trial implant 502 can be used as a reference to size an implant 40 which will be fitted into the joint space. When the trial implant 502 is inserted in the facet joint, the shaft 504 extends outward from the facet joint 28.

The trial member 500 can include a notch 512 on the proximal end of the shaft 504 to secure the trial member 500 to a tool 400 via a retention member. The trial implant 502 can comprise a disk-like member having an aperture 508. The trial implant 502 can have a curved or cupped shape to facilitate positioning between the articular processes 20, 22. In some embodiments, the trial implant 502 may have different shapes, sizes and thicknesses for use with different sized vertebra.

Some embodiments comprise tools and methods for creating holes or lumens through one or more bone portions such as the articular processes 20, 22 of the vertebra to facilitate implantation of the implant 40. In some embodiments, the holes or lumens have a curved or non-linear configuration. The curved or non-linear configuration allows relatively greater penetration through the thicker portions of the articular process(es) and therefore the articular process(es) may be less likely to fracture during formation of the hole or lumen. While various instruments have been proposed for drilling into and through bone, including for example, the curved drills described in U.S. Pat. Nos. 5,700,265, 6,419,678, and 6,607,530, herein incorporated by reference in their entirety, the subject tool offers the benefits of lumen formation through the articular processes within the limited surgical access available about the vertebra. The devices described herein may utilize one or more curved punch members or curved drills that rotate about an axis that is transverse to the movement plane of the curved punch or curved drill member. Unlike traditional orthopedic procedures that require unimpeded access to the surgical site due to the longitudinally-oriented surgical tools, the curved punch or curved drill members also permit access using a limited space or cavity around the articular processes. As used herein, the terms "lumen-forming" and "lumen formation" refer to the creation of a hole, passageway or indentation generally such as by, for example, piercing, punching, boring, puncturing, or drilling.

Figure 14:
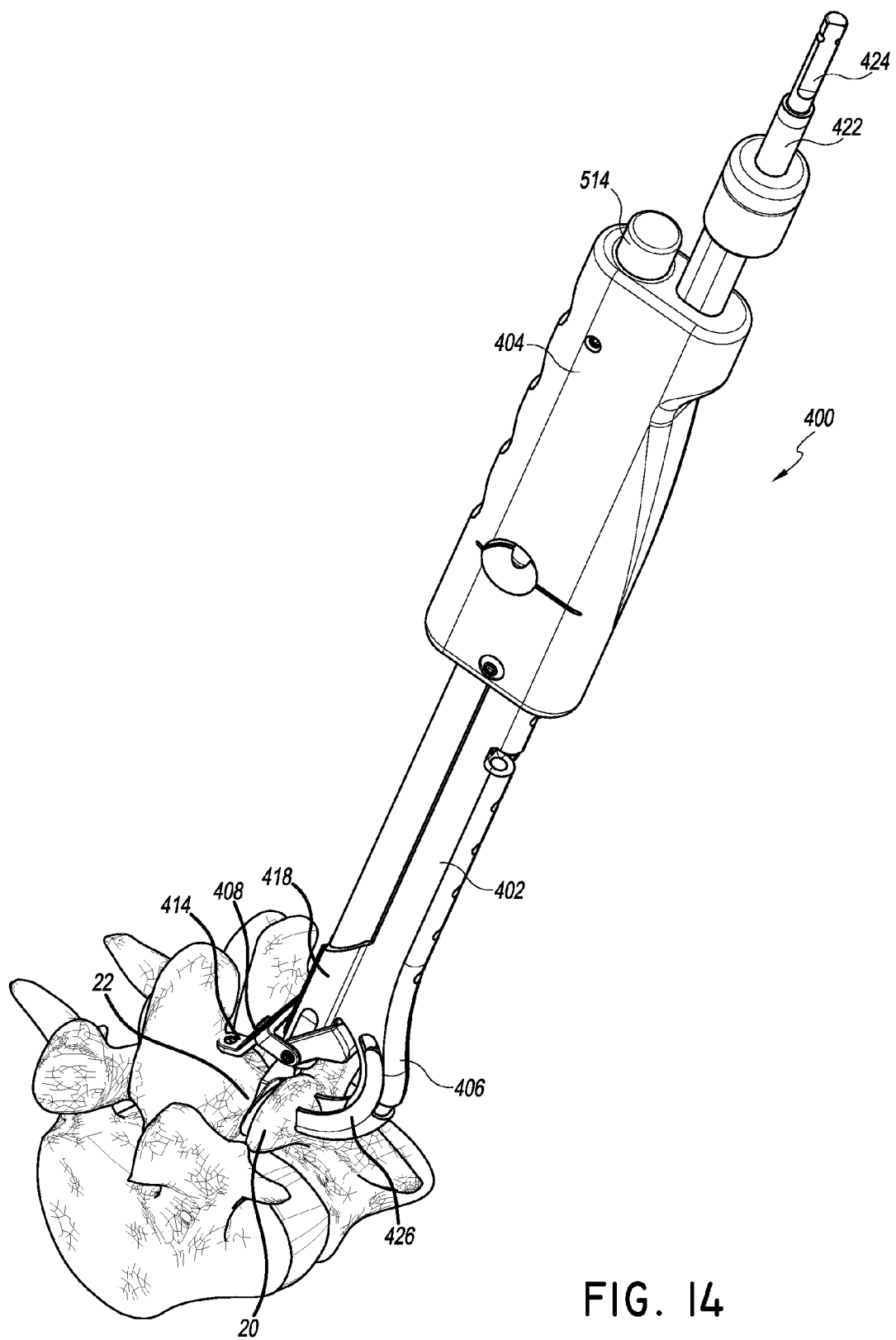
FIG. 14 is a schematic view of one embodiment of a tool guided over the trial member of FIG. 13.

FIG. 14 shows the tool 400 coupled to the trial member 500. One embodiment of the tool 400, shown in FIG. 14, comprises a shaft 402 with a proximal handle 404 and a distal arm guide 406. The arm guide 406 contains a lumen-forming arm 410 (not shown) that can be moved in the proximal-distal direction by manipulation of a proximal actuator 422. The distal portion also comprises an opposing target member 408 having a target plate 414. The lumen-forming arm 410 comprises a rotating drill bit 412 (not shown) that can be connected to a drill motor by a drill coupler 424 disposed toward the proximal end of the tool 400. A trial member 500 with a trial implant 502 can be coupled to the tool 400. The trial member 500 can be at least partially supported on the tool 400 by a frame 418 and the proximal handle 404. In some embodiments, the trial member 500 can be secured to the tool 400 by a retention member, which can be released by a release button 514.

The lumen-forming arm 410 can be slideably contained within the shaft 402 and the arm guide 406. The lumen-forming arm 410 can be moved between an advanced configuration, and a retracted configuration, by a proximal actuator 422 that moves the lumen-forming arm 410 axially along the shaft 402 of the tool 400. In the embodiment shown, manipulation of the actuator 422 causes a longitudinal movement of the lumen-forming arm 410. The lumen-forming arm 410 can be straight or curved or a combination of these shapes. The lumen-forming arm 410 may be stiff, bendable, or partially stiff and partially bendable.

In some embodiments, the lumen-forming arm 410 can be sized to be able to pass through the articular processes 20, 22 of the spine and the resulting hole is sized for a flexible member 30 and/or band 140, 240 to be inserted. The lumen-forming arm 410 can have a diameter in the range of about 1 mm to 5 mm, preferably about 2 mm to 4 mm, and most preferably about 3 mm. At an end of the rotating drill bit 412 can be a drill bit tip 413 (not shown) with a cutting surface for creating the lumen in the facets.

A target member 408 having a target plate 414 can be connected to the frame 418. The target plate 414 is in the path of travel of the lumen forming arm 410 and thus the position of the target plate 414 against an articular process 22 can provide indication to the user of where the lumen forming arm 410 will emerge from the articular processes 20, 22 during the drilling procedure. The target member 408 can advantageously help the user avoid neural or other structures in and around the articular process 22 by visualizing and understanding the trajectory of the lumen forming arm 410 through the articular processes 20, 22. In some embodiments, the target member 408 can provide some stabilization of the articular processes 20, 22 as the lumen forming arm 410 passes or cuts through the bone.

The tool 400 can further comprise a trial member 500 that can be coupled to the handle 404. The trial member 500 can comprise a shaft 504 that is connected by retention member to the tool 400. Preferably, the retention member allows the trial member 500 to be detached from and attached to the facet drill tool 400 with ease. With the trial member 500 in place and the trial implant 502 in the facet joint 28 as shown in FIG. 13, the tool 400 can be guided over the shaft 504 until the retention member engages the notch 512 to lock the trial member 500 to the tool 400. The trial member 500 has a trial implant 502 at the distal end. The trial implant 502, in turn, can comprise a disk-like member and an aperture 508 that is lined up with the lumen-forming arm 410 to allow the drill bit tip 413 of the lumen-forming arm 410 to penetrate through the bones and through the aperture 508. The trial implant 502 can have a curved or cupped shape to facilitate positioning between the articular processes 20, 22. In some embodiments, the trial implant 502 may have different shapes, sizes and thicknesses for use with different sized vertebra.

The tool 400 may be used by positioning the anchor portion 426 of an arm guide 406 against one bone portion such as the articular process 20 and positioning the target plate 414 against another bone portion, such as the articular process 22. The tool 400 can be rotated axially relative to the trial member 500 to adjust for variations in the native anatomy of the patient. The surgeon may select a particular rotational and/or angular approach to the surgical site, depending upon the particular anatomy of the patient, the extent and location of damage or injury, prior surgery, and other factors known in the art. Additional embodiments and method related to drilling holes in bones can be found in U.S. Patent Publication No. 2011/0040301 (application Ser. No. 12/859,009, filed Aug. 18, 2010).

In some embodiments, the trial member 500 can rotate about its longitudinal axis while coupled to the tool 400 to accommodate variations in the shapes and positions of the articular processes 20, 22. The aperture 508 can be sufficiently large to allow the lumen-forming arm 410 to pass through the aperture 508 even when the trial member 500 is at an angle to the lumen-forming arm 410.

Alternative embodiments and methods of use of various tools are described in commonly owned US. Patent Publication No. 2011/0040301 (U.S. application Ser. No. 12/859,009, filed Aug. 18, 2010), which is incorporated by reference. Accordingly, the device and methods herein can be combined with the devices and methods disclosed in other applications incorporated by references.

Figure 15A:
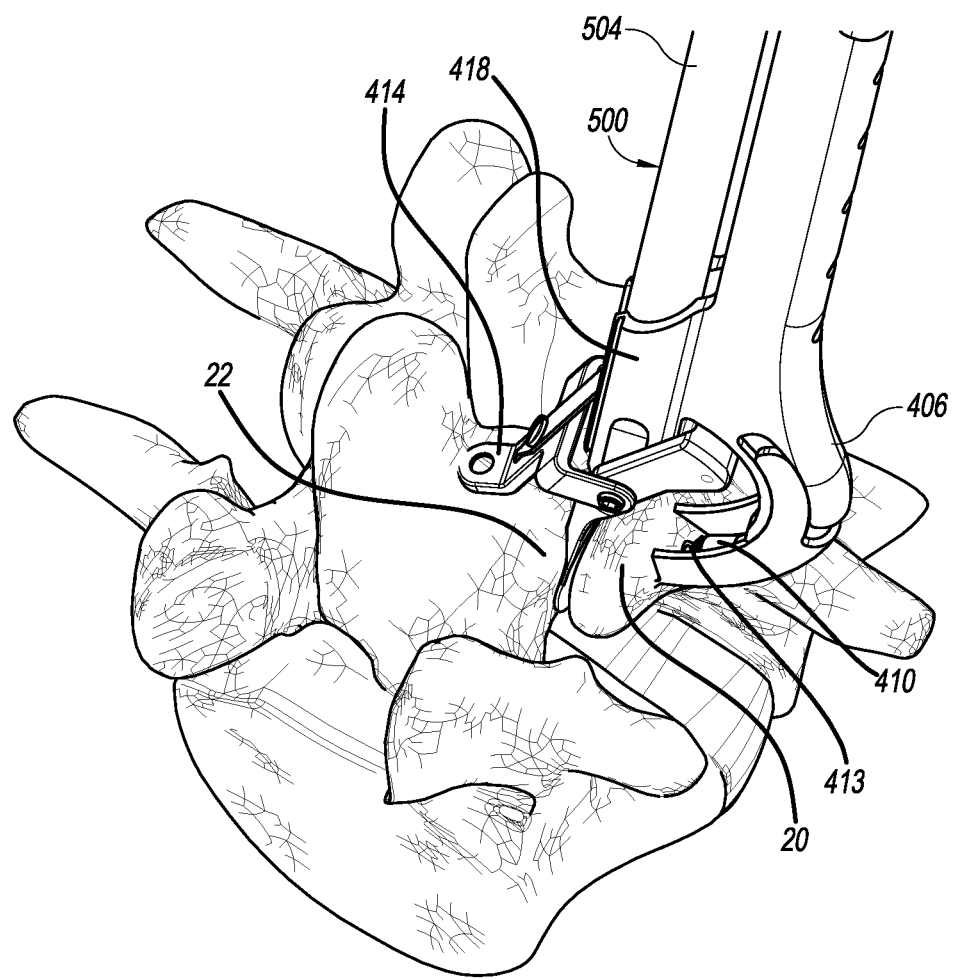
FIGS. 15A-15B are posterior perspective views of a portion of the vertebral column depicting a method of using the tool of FIG. 14 to drill through the facet joint.
Figure 15B:
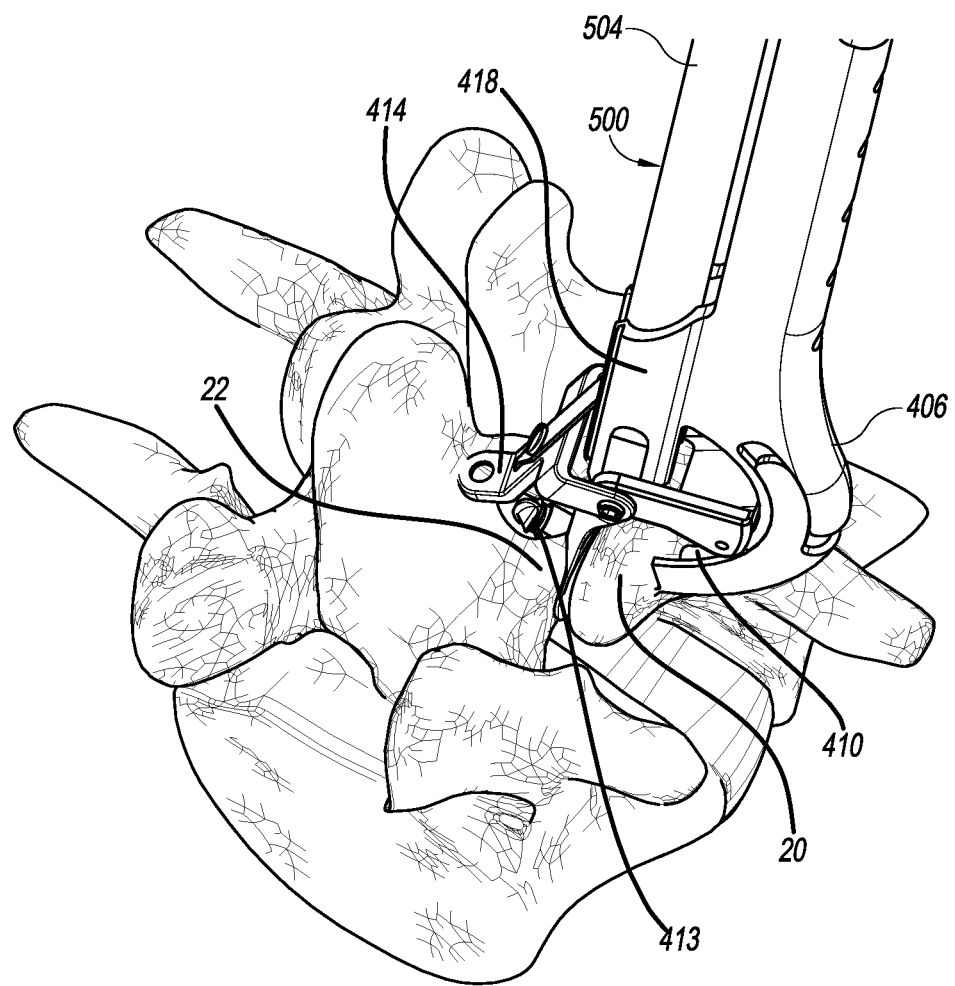

As shown in FIGS. 15A and 15B, the tool 400 can be used to drill through the facet joint thereby forming a lumen that extends across the facet joint. When the tool 400 is actuated, the drill bit tip 413 can be extended to cut the lumen in the articular process 20. The lumen-forming arm 410 can extend through the aperture 508 in the trial implant 502. Then the lumen-forming arm 410 can continue to extend to the target plate 414 of the opposing target member 408 to cut a lumen in the articular process 22. Once the curved hole is formed, the lumen-forming arm 410 can be retracted back through the lumen in the articular processes 20, 22.

Figure 16A:
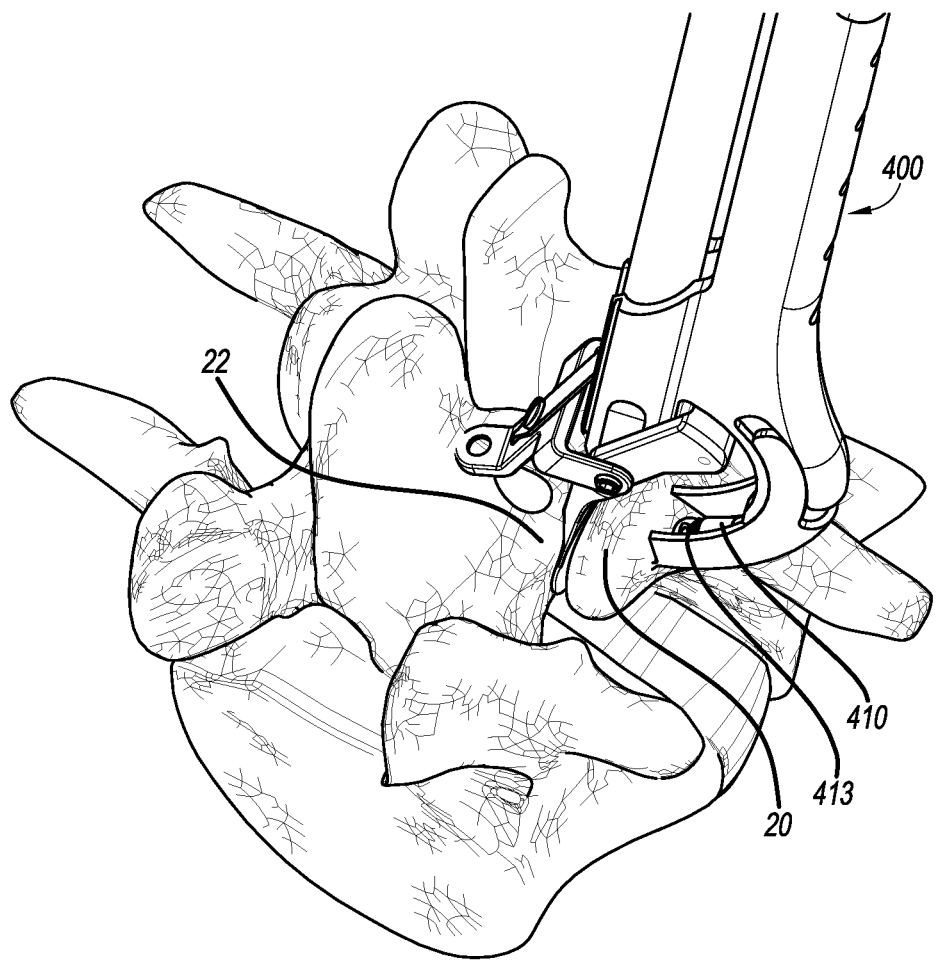
FIGS. 16A-16B are posterior perspective views of a portion of the vertebral column depicting a method of passing a flexible member through the facet joint.
Figure 16B:
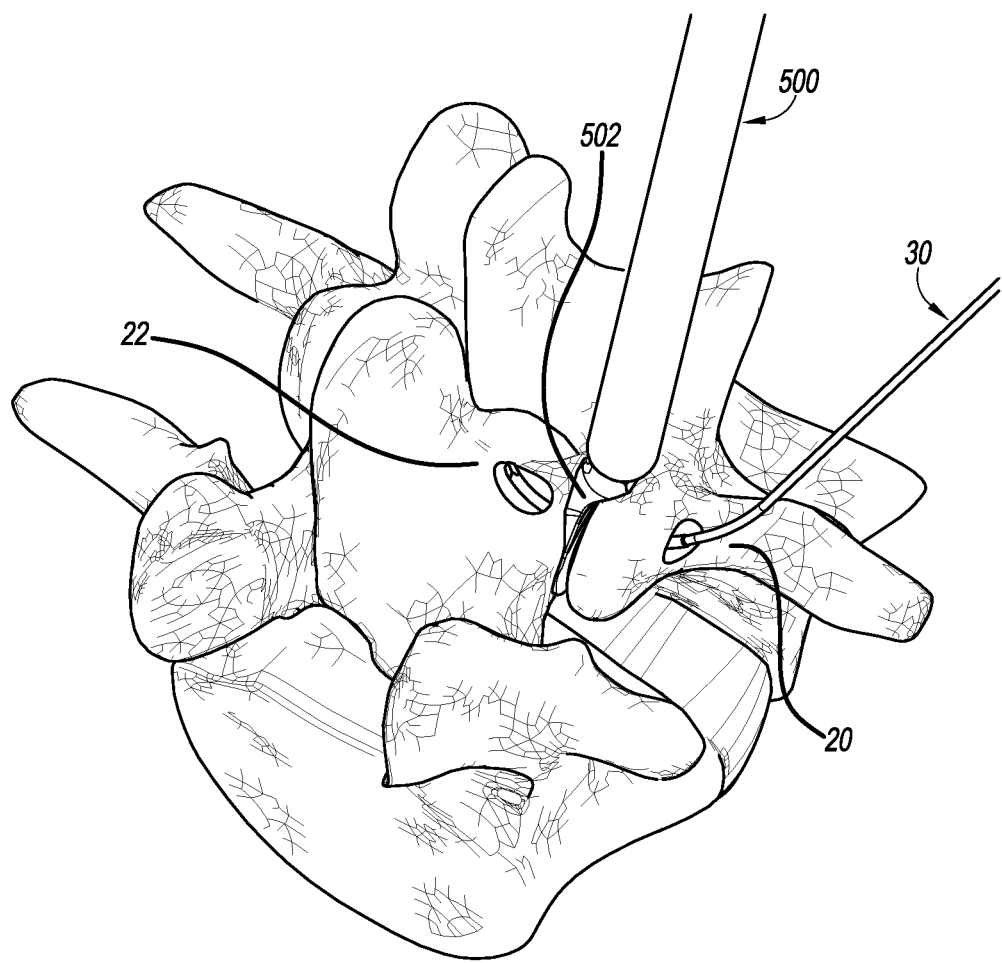

As shown in FIGS. 16A and 16B, the flexible member 30 can be passed through the lumen of the first articular process 20, through the aperture 508 in the trial implant 502, and through the second articular process 22. In one arrangement, the proximal end portion of the flexile member 30 can be inserted into the lumen of superior articular process SAP2A of vertebra V2, through the aperture 508 in the trial implant 502, and through the lumen of inferior articular process IAP1A of vertebra V1. FIG. 16A shows that the flexible member 30 can be inserted through aperture 508 in the trial implant 502 and the through the lumens of the facets while the tool 400 is in place. For example, the lumen-forming arm 410 can guide the flexible member 30 through the lumens in the articular processes 20, 22. In some embodiments, the flexible member 30 is inserted through the lumens as the drill bit tip cuts the lumen. FIG. 16B shows the flexible member 30 can be inserted through the aperture 508 in the trial implant 502 and the through the lumens of the facets after the tool 400 is removed. The flexible member 30 can be coupled to a curved needle 32 shown in FIG. 17 or other guiding device to facilitate insertion of the flexible member 30 through the lumens of the facets. In both FIGS. 16A and 16B, the trial member 500 remains within the patient and the trial implant 502 remains within the facet joint 28 while the flexible member 30 is threaded through the articular processes 20, 22. One end of the flexible member 30 can extend beyond the first articular process 20 and the other end of the flexible member 30 can extend beyond the second articular process 22 as shown in FIG. 17.

Figure 17:
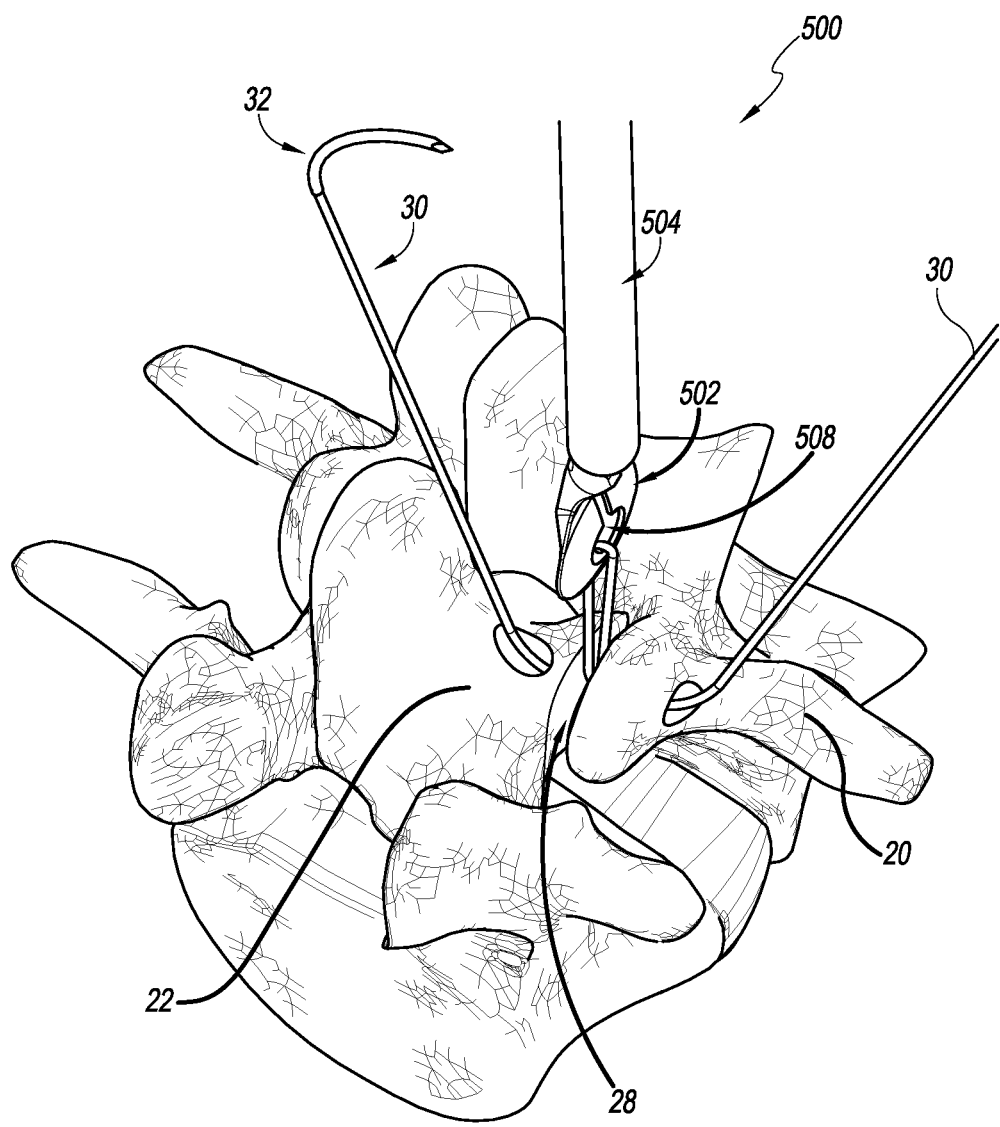
FIG. 17 is a posterior perspective view of a portion of the vertebral column depicting a method of pulling the flexible member of FIGS. 16A-16B out of the facet joint using the trial member.

FIG. 17 shows the trial implant 502 can be withdrawn from the facet joint 28. The flexible member 30 is retained within the aperture 508 of the trial implant 502 during this step. The shaft 504 can be pulled away from the facet joint 28, thereby withdrawing the trial implant 502. Withdrawing the trial implant 502 causes the flexible member 30 to extend outward and beyond the facet joint 28 as shown. The flexible member 30 has sufficient length to extend through both facets as the trial implant 502 is withdrawn from the facet joint 28. The ends of the flexible member 30 are drawn inward, toward the facet joint 28 as the trial implant 502 is withdrawn. As shown, the ends of the flexible member 30 extend beyond the lumens in the articular processes 20, 22 after the trial implant 502 is withdrawn.

Figure 18:
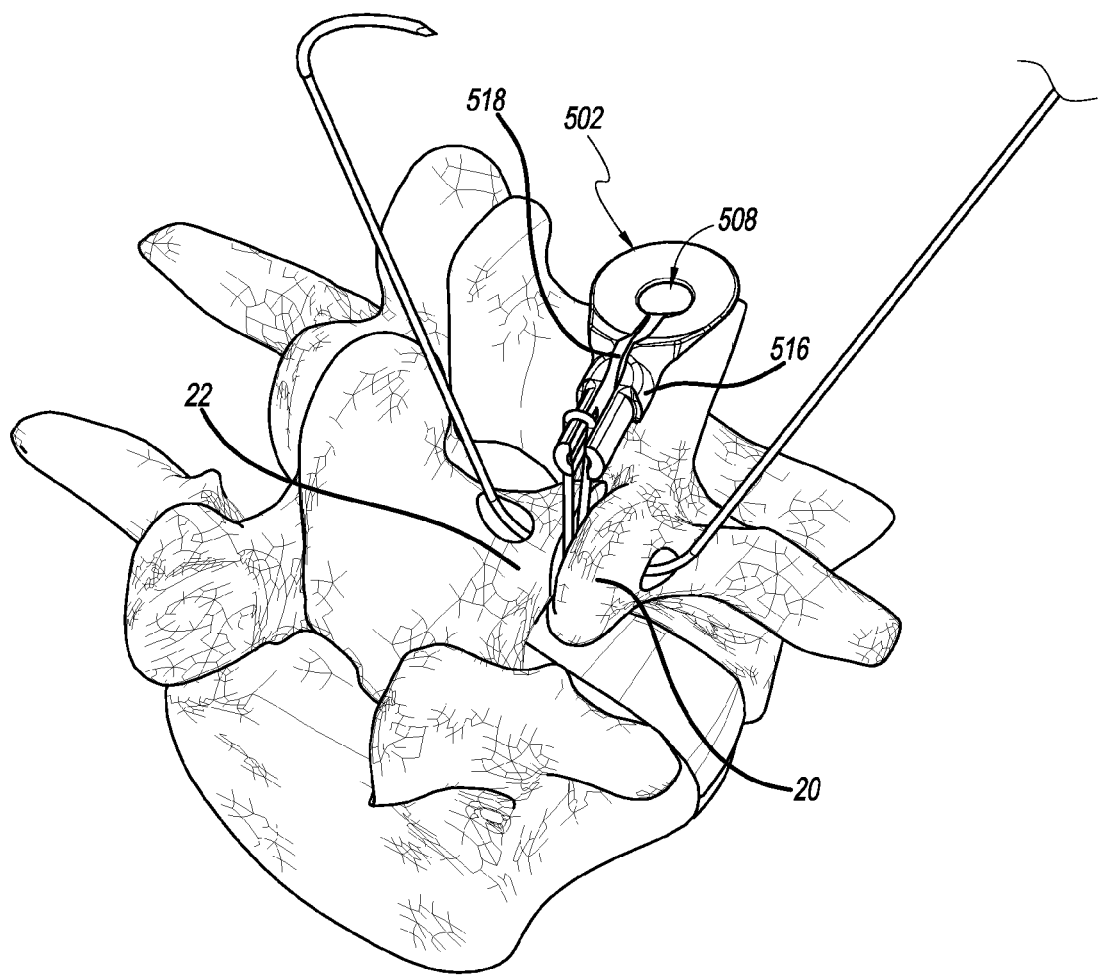
FIG. 18 is a posterior perspective view of a portion of the vertebral column depicting a method of disassembling the trial member.

As shown in FIG. 18, the trial member 500 can be disassembled. In some embodiments, the trial implant 502 is decoupled from the shaft 504. The stem 516 of the trial implant 502 can be releasably retained within the shaft 504 during any or all of the previous steps. The stem 516 can include a slot 518 extending from an edge of the stem 516 to the aperture 508. The slot 518 may be linear or non-linear. A non-linear slot may prevent accidental disengagement between the trial implant 502 and the flexible member 30. In some methods, the trial implant 502 can be rotated 90 degrees as shown in FIG. 18 to facilitate removal of the flexible member 30 from the trial implant 502. The flexible member 30 can be passed from the aperture 508 through the slot 518 toward the edge of the stem 516. The flexible member 30 can be disengaged from the aperture 508 and the slot 518 thereby freeing the flexible member 30 from the trial implant 502. In some embodiments, the trial implant 502 includes an engagement feature extending from the edge of the trial implant 502 to the aperture 508. The engagement feature may be a slot, such as slot 518. In some embodiments, the engagement feature is formed only after the trial implant 502 is decoupled from the shaft 504. For instance, slot 518 can be formed only when the stem 516 is in an expanded state in which the two halves of the stem 516 are spaced apart. Other designs are contemplated to permit the flexible member 30 from disengaging from the trial implant 502.

Figure 19:
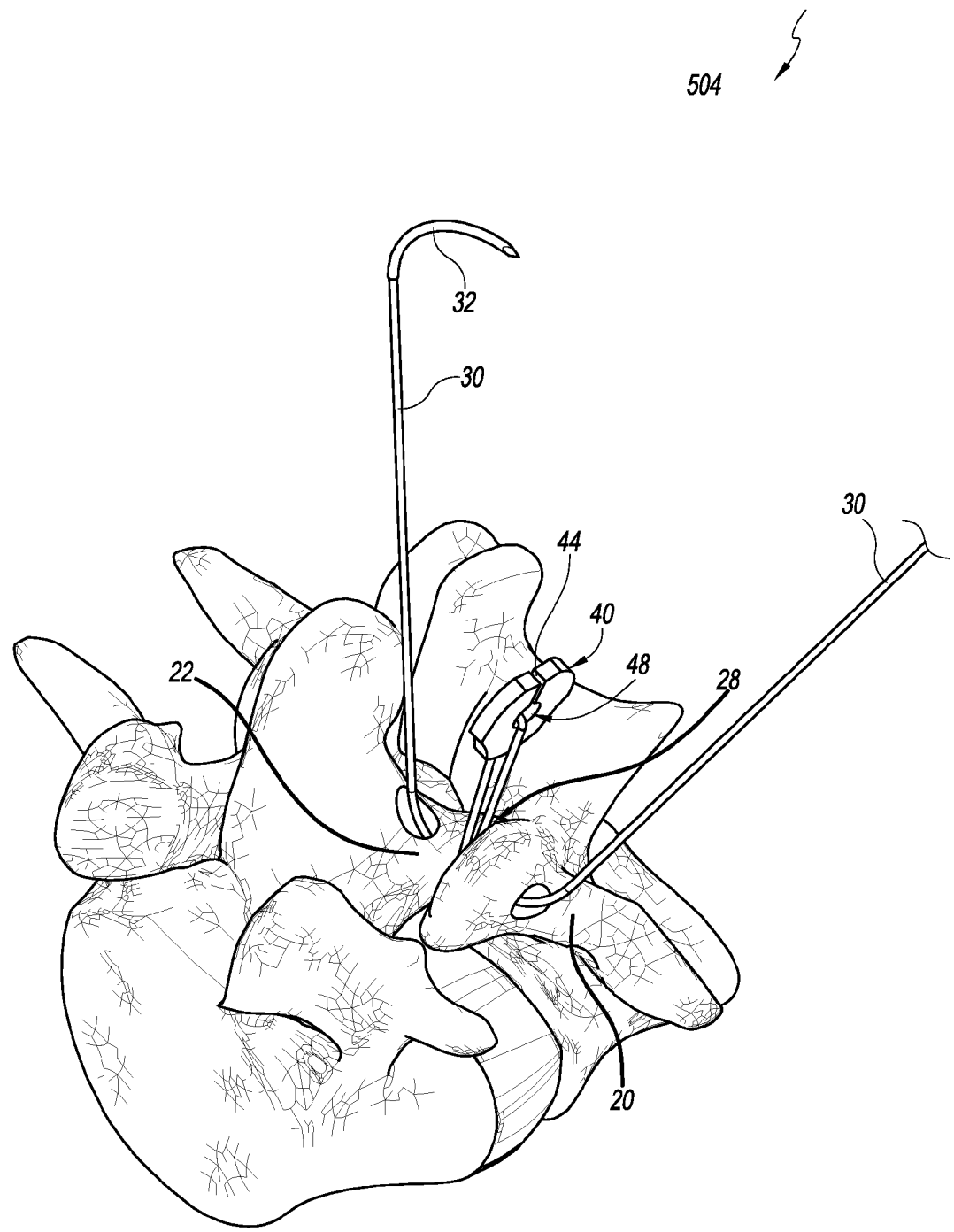
FIG. 19 is a posterior perspective view of a portion of the vertebral column depicting a method of loading an implant onto the flexible member.

FIG. 19 shows the implant 40 coupled to the flexible member 30. A portion of the flexible member 30 extending outward and beyond the facet joint 28 can be coupled to the implant 40. In some embodiments, the implant 40 comprises an engagement feature extending from the edge of the implant 40 to an aperture 48. The engagement feature may be a slot 44, which may be linear or non-linear. A non-linear slot may prevent accidental disengagement between the implant 40 and the flexible member 30. Other embodiments are contemplated to engage the flexible member 30 with the implant 40. The flexible member 30 can be inserted from the slot 44 to the aperture 48 to couple the implant 40 to the flexible member 30.

The implant 40 comprises a body with a least two faces, a first face adapted to contact a first bone such as the articular surface of one facet of the facet joint and a second face adapted to contact a second bone such as the articular surface of the other facet. The aperture 48 can be sized and configured to accept a retaining member, such as the retaining members described in U.S. Pat. No. 7,846,183 (U.S. application Ser. No. 10/865,073, filed Jun. 10, 2004). The aperture 48 can be sized and configured to accept a band, such as the bands described herein and in U.S. Publication No. 2012/0221060 (U.S. application Ser. No. 13/033,791, filed Feb. 24, 2011).

In some embodiments, the implant 40 has a generally circular profile and is sized to fit generally within the joint capsule of the facet joint 28. In some embodiments, the implant 40 can be, for example, substantially disc shaped. In other embodiment of the invention, the implant 40 can have any of a variety of profiles, including but not limited to square, rectangle, elliptical, oval, star, polygon or combination thereof. In some embodiments, an implant 40 having the desired shape is selected from an array of implants after radiographic visualization of the articular processes and/or by radio-contract injection into the facet joint to visualize the joint capsule.

In some embodiments, the implant 40 has a diameter of about 4 mm to about 30 mm. In another embodiment, the implant 40 has a diameter of about 5 mm to about 25 mm. In still another embodiment, the implant 40 has a diameter of about 10 mm to about 20 mm. In some embodiments, the implant 40 has a cross-sectional area of about 10 $mm^2$ to about 700 $mm^2$. In another embodiment, the implant 40 has a cross-sectional area of about 25 $mm^2$ to about 500 $mm^2$. In still another embodiment, the implant 40 has a cross-sectional area of about 20 $mm^2$ to about 400 $mm^2$, and preferably about 25 $mm^2$ to about 100 $mm^2$.

The implant 40 has a thickness generally equal to about the anatomic spacing between two facets of a facet joint. In some embodiments, the implant 40 generally has a thickness within the range of about 0.5 mm to about 3.0 mm. In some embodiments, the implant 40 has a thickness of about 1 mm to about 2 mm. In some embodiments, the implant 40 has a thickness of about 0.5 mm to about 1.5 mm. In some embodiments, the thickness of the implant 40 is non-uniform within the same implant. For example, the thickness of the implant 40 can be increased around the entire outer edge, along at least one and, as illustrated, both faces. In some embodiments, only a portion of the edge on one face of the implant 40 has a thickness that is greater than the thickness of a central region, and, optionally, also thicker than the typical anatomic spacing between two facets of a facet joint. An increased edge thickness may resist lateral displacement of the prosthesis out of the facet joint.

In some embodiments of the invention, the implant 40 is configured to provide an improved fit with the articular process and/or joint capsule. For example, the implant 40 can have a bend, angle or curve to generally match the natural shape of an articular facet. The implant 40 may be rigid with a preformed bend. Alternatively, the implant 40 may be sufficiently malleable that it will conform post implantation to the unique configuration of the adjacent facet face. In certain embodiments, the implant 40 is configured to be implanted between the articular processes and/or within the joint capsule of the facet joint, without securing of the implant to any bony structures. Such embodiments can thus be used without invasion or disruption of the vertebral bone and/or structure, thereby maintaining the integrity of the vertebral bone and/or structure.

The implant 40 can be similar to, and have similar features to the embodiments of the prosthesis shown and described in commonly owned U.S. Pat. No. 7,846,183 (application Ser. No. 10/865,073, filed Jun. 10, 2004), which is incorporated herein by reference in its entirety. The implant 40 can be implanted and deployed to restore the space between facets of a superior articular process of a first vertebra and an inferior articular process of an adjacent vertebra. As described herein, the implant 40 can be deployed to help stabilize adjacent bone portions, such as adjacent facets of a facet joint. A porous surface can allow bone to grow into or attach to the surface of the implant, thus securing the implant to the bone. In one embodiment, an adhesive or sealant, such as a cyanoacrylate, polymethylmethacrylate, or other adhesive known in the art, is used to bond one face of the implant to an articular surface.

The implant can include a first side and a second side. The first side and/or the second side can be, for example, convex, concave, or flat. The first side of the implant can be concave, convex, or flat, and the second side of the implant can be concave, convex, or flat. For example, the first side can be concave and the second side concave, the first side can be concave and the second side convex, etc.

In some embodiments, at least a portion of the implant 40 can be formed of allograft. In some embodiments, at least a portion of the implant 40 can be formed of artificial materials, such as, for example, titanium or PEEK. In some embodiments, the implant 40 can be deployed to deliver and/or release a substance. In some embodiments, the substance can have therapeutic properties, for example, a medication. In some embodiments, the substance is an adhesive. The implant 40 can include the same materials as the flexible band, describe herein. In some embodiments, the implant 40 can increase the stability of a vertebra and/or the flexible band, describe herein.

As described in these applications, U.S. Patent Publication Nos. 2012/0221049 (U.S. application Ser. No. 13/403, 698, filed Feb. 23, 2012) and 2012/0221060 (U.S. application Ser. No. 13/033,791, filed Feb. 24, 2011) in certain embodiments it is useful to dispose the implant 40 between the first and second bone portions before stabilizing the two bone portions and/or performing other procedures. Certain aspects of the described herein involve facilitating the insertion of the implant 40 between the bone portions. Accordingly, the device as methods herein can be combined with the devices and methods disclosed in other applications incorporated by references.

Figure 20A:
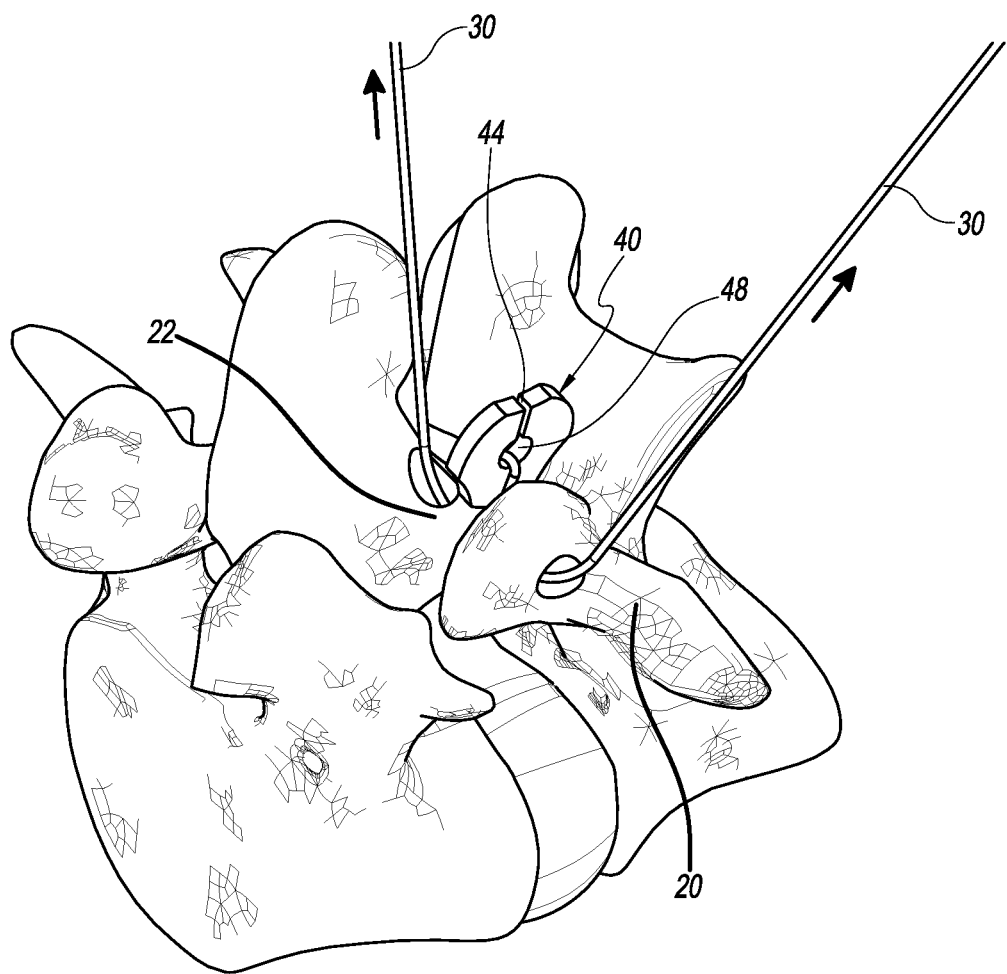
FIGS. 20A-20B are posterior perspective views of a portion of the vertebral column depicting a method of pulling the implant of FIG. 19 into the facet joint by making the flexible member taut.
Figure 20B:
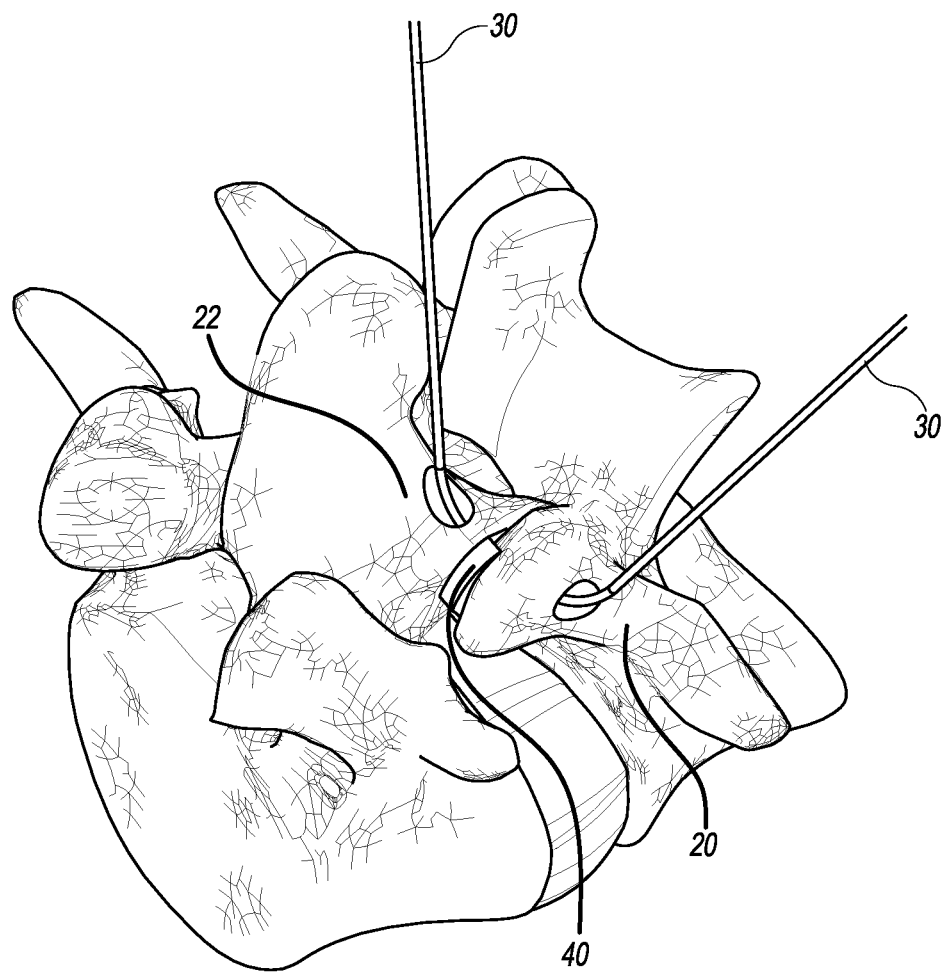

FIG. 20A shows the implant 40 being inserted into the facet joint. To reduce the implant 40 into the facet joint, tension can be applied to one or both ends of the flexible member 30. The slot 44 can be oriented away from the facet joint 28 to prevent accidental disengagement of the flexible member 30 from the implant 40. The tension takes up slack in the flexible member 30, urging the implant 40 into the joint space. Tension can be applied until the implant 40 is held taut by the flexible member 30. The implant 40 can be positioned such that the aperture 48 forms a path between the first bone portion and the second bone portion, as illustrated in FIG. 20B. In some embodiments, the flexible member 30 is secured to maintain the position of the implant 40. In some embodiments, the ends of the flexible member 30 are secured to each other or to other objects such as anchors, tacks, or bones. In some embodiments, the ends of the flexible member 30 are tied. In some embodiments, the flexible member 30 is removed. In some embodiments, the ends of the flexible member 30 are cut.

Figure 21:
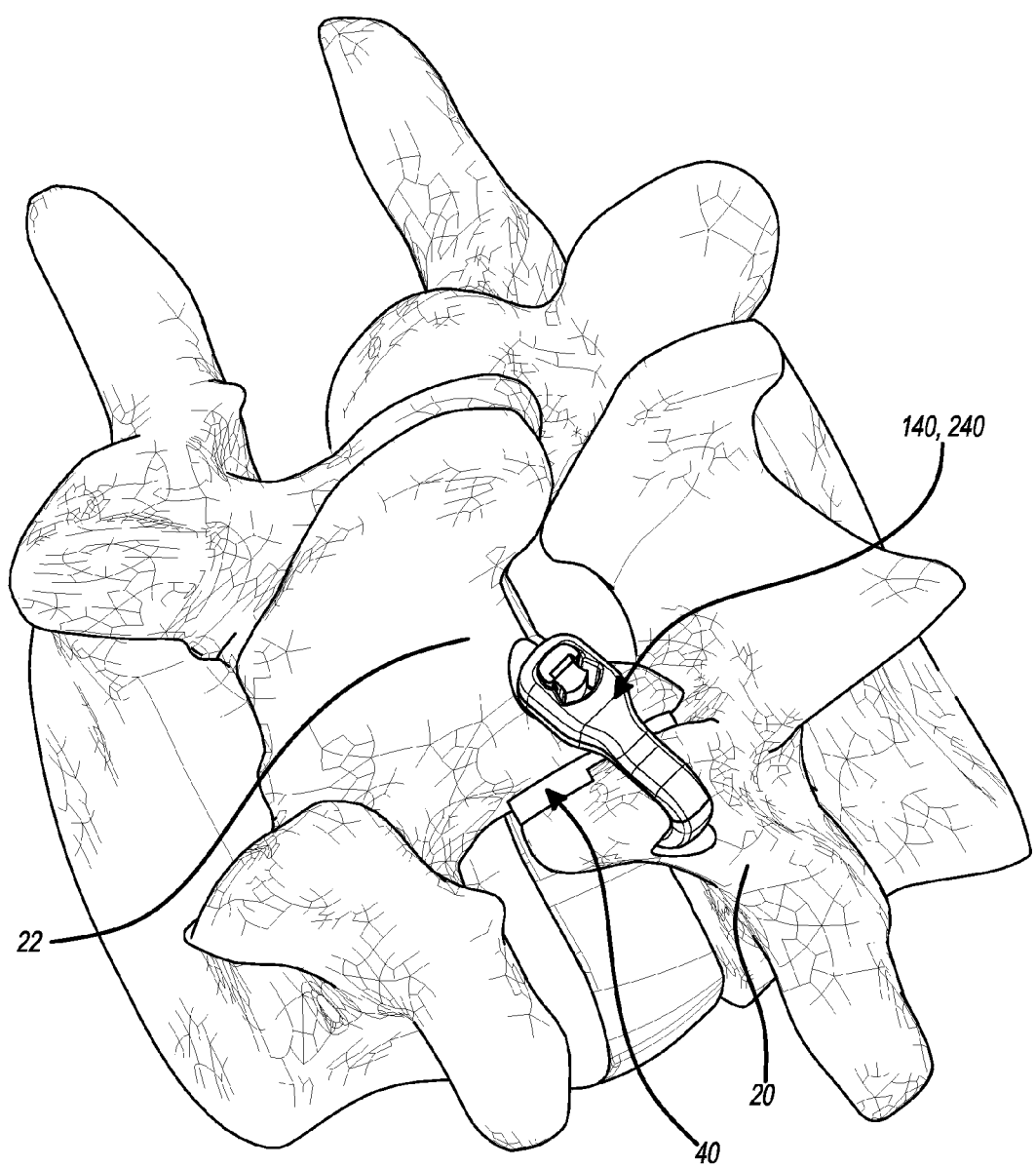
FIG. 21 is a posterior perspective view of a portion of the vertebral column depicting a method of cinching the facet joint closed using a flexible fastening band.

As shown in FIG. 21, the facet joint can be stabilized using a band 140, 240 as described herein. In some embodiments, the band 140, 240 can follow the path of the flexible member 30. In some embodiments, the flexible member 30 is removed prior to insertion of the band 140, 240. In other embodiments, the flexible member 30 is removed after to insertion of the band 140, 240. The band 140, 240 can be extended through the lumen of the first facet, the aperture 48 of the implant 40, and through the lumen in the second facet. The proximal end 142, 242 of the band 140, 240 can be advanced through a fastening mechanism 150, 250 until the two facets are stabilized.

FIG. 22 illustrates is a block diagram of a kit for inserting an implant into a facet joint according to an embodiment. The kit 600 can include the tool 400 as described herein. The kit 600 can include the trial member 500 including the trial implant 502 and the shaft 504. The kit 600 can include the flexible member 30. The kit can include the implant 40. In some embodiments, the kit includes two of the components selected from the group of the tool 400, the trial member 500, the flexible member 30 and the implant 40. In some embodiments, the kit includes three of the components selected from the group of the tool 400, the trial member 500, the flexible member 30 and the implant 40. In some embodiments, the kit includes all of the following components: the tool 400, the trial member 500, the flexible member 30 and the implant 40. In some embodiments, the kit includes multiple implants 40 (e.g., two, three, four, a plurality). In some embodiments, the kit includes multiple trial members 500 (e.g., two, three, four, a plurality). In some embodiments, the kit includes multiple trial implants 502 (e.g., two, three, four, a plurality).

In some embodiments, a method of placing an implant into a facet joint of the spine is provided. The method can include the step of forming a hole across the facet joint. The method can include the step of passing a flexible member through the hole and across the facet joint. The method can include the step of bringing the flexible member out of the facet joint. The method can include the step of coupling an implant to the flexible member. The method can include the step of tightening the flexible member to reduce into the implant into a joint space.

The method can include the step of cutting the flexible member. The method can include the step of tying cut ends of the flexible member together. In some embodiments, the flexible member is a suture. In some embodiments, the implant includes a hole for receiving the flexible member. In some embodiments, the implant includes a slot for receiving the flexible member. In some embodiments, the implant includes allograft or an artificial material. In some embodiments, the implant is sized to fit into the joint space. In some embodiments, the step of forming a hole across the facet joint comprises drilling a hole. In some embodiments, the step of bringing the flexible member out of the facet joint comprises bringing the flexible member out at a joint line. The method can include the step of inserting a trial implant into the joint space before forming a hole across the facet joint. The method can include the step of withdrawing the trial implant out of the joint space to bring the flexible member out of the facet joint. The method can include the step of inserting a flexible retention member through the facet joint and the implant and using the flexible retention member to secure the facet joint.

In some embodiments, a method of placing an implant in a spine facet joint is provided. The method can include the step of drilling a hole across the facet joint. The method can include the step of removing the drill. The method can include the step of leaving behind a trial/targeting device in the joint space. The method can include the step of passing a suture through the hole and across the facet joint. The method can include the step of bringing the suture out of the facet joint at a joint line by removing the trial/targeting device. The method can include the step of removing the suture from the trial/targeting device by passing it through a slot in the trial/targeting device. The method can include the step of placing an implant with a hole and slot over the suture. The method can include the step of pulling the suture tight to reduce implant into the joint space. In some embodiments, the implant comprises artificial material and/or allograft. In some embodiments, the implant is configured and sized to fit into the joint space.

In some embodiments, a device for placement in a spine facet joint is provided. The device can include a body that is sized to fit in the facet joint of a spine. In some embodiments, the body is formed from artificial materials, allograft or a combination thereof. In some embodiments, the body has a hole for receiving a suture or flexible fixation member. In some embodiments, the body has a slot so that it can be placed over a portion of the suture or flexible fixation member.

In some embodiments, a kit for placement of an implant into a spine facet joint is provided. The kit can include a trial member with an opening. The kit can include a drill configured to form an opening between two bone portions and the trial member inserted between the two bone portions. The kit can include an implant with an opening. The kit can include a flexible member. The kit can include a flexible fastening band through with fastener. In some embodiments, the implant comprises an allograft.

It should be appreciated that the methods and devices described herein for placing an implant into a joint or between two bone portions are not limited to fusion applications and/or the fusion devices described herein. For example, the methods and devices described herein for placing an implant into a joint or between two bone portions can be used with fixation devices that utilized flexible fasteners of different configuration and/or fasteners that are not flexible (e.g., rods, screws, and/or clamps) that extend across the joint or between bone portions.

In addition, methods and devices described herein for placing an implant into a joint or between two bone portions can also be used in non-fusion applications. For example, U.S. Pat. Nos. 7,846,183 and/or 8,740,949 (which are incorporated by reference herein) disclose various devices and methods for the augmentation and restoration of vertebral facet joints. Several embodiments involve the insertion of implant (e.g., a disk) into the facet joint. Several embodiments include a hole or slot in the implant and/or a flexible member that can extend across an opening formed in the facet joint and the implant. In such embodiments, the techniques and devices described herein for advancing a flexible member through the facet joint and then using the flexible member to urge the implant into the facet joint can be used.

It should also be appreciated that the methods and devices herein are not limited to the facet joint but can also be used to insert an implant between to bone portions and/or other joints in the body.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while several variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. It should be understood that various features and aspects of the disclosed embodiments can be combined with, or substituted for, one another in order to form varying modes of the disclosed invention. For all the embodiments described above, the steps of the methods need not be performed sequentially. Thus, it is intended that the scope of the present invention herein disclosed should not be limited by the particular disclosed embodiments described above, but should be determined only by a fair reading of the claims that follow.

What is claimed is:

1. A method of placing an implant between a first bone portion and a second bone portion, the method comprising:
   forming a lumen in a first bone portion;
   forming a lumen in a second bone portion;
   inserting a trial implant between the first bone portion and the second bone portion;
   inserting a portion of a flexible member through the lumen in the first bone portion, through the trial implant, and through the lumen in the second bone portion;
   withdrawing the trial implant and the flexible member from between the first and second bone portions;
   coupling the implant with the flexible member; and
   advancing the implant between the first and second bone portions,
   wherein the first bone portion is a first articular process and the second bone portion is a second articular process.

2. The method of claim 1, wherein the step of coupling the implant with the flexible member comprises passing the flexible member through a hole in the implant.

3. The method of claim 1, wherein the step of coupling the implant with the flexible member comprises passing the flexible member through a slot extending from the edge of the implant.

4. The method of claim 1, wherein the implant comprises an allograft.

5. The method of claim 1, wherein the implant is sized to fit into a joint space between the first bone portion and the second bone portion.

6. The method of claim 1, wherein forming the lumen in the first bone portion comprises drilling a hole.

7. The method of claim 1, wherein advancing the implant between the first and second bone portions comprises applying tension to both ends of the flexible member.

8. The method of claim 1, wherein the trial implant is inserted between the first bone portion and the second bone portion before forming the lumen in the first bone portion and forming the lumen in the second bone portion.

9. A method of placing an implant between a first bone portion and a second bone portion, the method comprising:
   forming a lumen in a first bone portion;
   forming a lumen in a second bone portion;
   inserting a trial implant between the first bone portion and the second bone portion;
   inserting a portion of a flexible member through the lumen in the first bone portion, through the trial implant, and through the lumen in the second bone portion;
   withdrawing the trial implant and the flexible member from between the first and second bone portions;
   coupling the implant with the flexible member; and
   advancing the implant between the first and second bone portions,
   wherein withdrawing the flexible member from between the first and second bone portion comprises bringing the flexible member out at a joint line.

10. The method of claim 9, wherein the implant comprises an allograft.

11. The method of claim 9, further comprising inserting the trial implant between the first bone portion and the second bone portion before forming the lumen in the first bone portion and forming the lumen in the second bone portion.

12. The method of claim 9, wherein advancing the implant between the first and second bone portions comprises applying tension to both ends of the flexible member.

13. A method of placing an implant between a first bone portion and a second bone portion, the method comprising:
   forming a lumen in a first bone portion;
   forming a lumen in a second bone portion;
   inserting a trial implant between the first bone portion and the second bone portion;
   inserting a portion of a flexible member through the lumen in the first bone portion, through the trial implant, and through the lumen in the second bone portion;
   withdrawing the trial implant and the flexible member from between the first and second bone portions;
   coupling the implant with the flexible member; and
   advancing the implant between the first and second bone portions;
   wherein the trial implant is inserted between the first bone portion and the second bone portion before forming the lumen in the first bone portion and forming the lumen in the second bone portion.

14. The method of claim 13, wherein the implant comprises an allograft.

15. A method of placing an implant between a first bone portion and a second bone portion, the method comprising:
   forming a lumen in a first bone portion;
   forming a lumen in a second bone portion;
   inserting a trial implant between the first bone portion and the second bone portion;
   inserting a portion of a flexible member through the lumen in the first bone portion, through the trial implant, and through the lumen in the second bone portion;

withdrawing the trial implant and the flexible member from between the first and second bone portions;

coupling the implant with the flexible member;

advancing the implant between the first and second bone portions; and inserting a flexible retention member through the first bone portion, the implant, and the second bone portion and using the flexible retention member to secure the first bone portion and the second bone portion.

16. The method of claim 15, wherein the flexible retention member comprises a ratchet.

17. The method of claim 15, wherein the implant comprises an allograft.

18. The method of claim 15, further comprising inserting the trial implant between the first bone portion and the second bone portion before forming the lumen in the first bone portion and forming the lumen in the second bone portion.

19. A method of placing an implant in a facet joint, the method comprising:

forming a hole across the facet joint;

inserting a trial implant in a joint space of the facet joint;

passing a flexible member through the hole and across the facet joint;

withdrawing the flexible member out of the facet joint at a joint line by withdrawing the trial implant;

coupling the implant with the flexible member; and pulling the ends of the flexible member to reduce the implant into the joint space.

20. The method of claim 19, wherein the implant comprises an allograft.

21. The method of claim 19, further comprising sizing the implant to fit into the joint space.

22. The method of claim 19, further comprising inserting the trial implant in the joint space before forming the hole across the facet joint.

\* \* \* \* \*